United States Patent [19]

Mandai et al.

[11] Patent Number: 5,919,668

[45] Date of Patent: *Jul. 6, 1999

[54] NON-REDUCING SACCHARIDE AND ITS PRODUCTION AND USE

[75] Inventors: Takahiko Mandai; Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/495,030

[22] Filed: Jun. 27, 1995

Related U.S. Application Data

[63] Continuation-in-part of application No. 08/253,171, Jun. 2, 1994, Pat. No. 5,472,863.

[30] Foreign Application Priority Data

Jun. 27, 1994 [JP] Japan .................................. 6-165815
Apr. 19, 1995 [JP] Japan .................................. 7-116583

[51] Int. Cl.$^6$ ............................. C12P 19/18; C12P 19/04; C12P 19/00; C07H 3/06
[52] U.S. Cl. .............................. 435/97; 435/72; 435/74; 435/95; 435/96; 435/98; 435/99; 435/100; 435/101; 536/123.1; 536/123.13
[58] Field of Search .................... 435/100, 101, 435/95, 96, 97, 99, 72, 74, 98; 536/123.1, 123.13

[56] References Cited

U.S. PATENT DOCUMENTS

| | | | |
|---|---|---|---|
| 4,521,252 | 6/1985 | Miyake et al. | 127/46.3 |
| 4,762,857 | 8/1988 | Bollin, Jr. et al. | 514/777 |
| 4,839,164 | 6/1989 | Smith | 424/64 |
| 5,026,566 | 6/1991 | Roser | 426/443 |
| 5,455,168 | 10/1995 | Maruta et al. | 435/201 |
| 5,472,863 | 12/1995 | Maruta et al. | 435/200 |

FOREIGN PATENT DOCUMENTS

| | | |
|---|---|---|
| 0606753 | 7/1994 | European Pat. Off. . |
| 154485 | 12/1975 | Japan . |
| 58-23799 | 2/1983 | Japan . |
| 58-72598 | 4/1983 | Japan . |
| 216695 | 12/1983 | Japan . |
| 2106912 | 4/1983 | United Kingdom . |
| WO92/03565 | 3/1992 | WIPO . |
| WO92/07947 | 5/1992 | WIPO . |

OTHER PUBLICATIONS

Patent Abstracts of Japan, JP 63–216492 A, Sep. 08, 1988.
Gekkan Food Chemical, Monthly Food Chemical pp. 67–72, Aug. 1992.
Wolfrom et al, Advances in Carbohydrate Chemistry, vol. 18, pp. 201–225, 1963.
Hoelzle et al, Increased Accumulation of Trehalose in Rhizobia . . . vol. 56, No. 10, pp. 3213–3215, Oct. 1990.

*Primary Examiner*—Francisco Prats
*Attorney, Agent, or Firm*—Browdy and Neimark

[57] ABSTRACT

In the production of non-reducing saccharides such as trehalose, alpha-glycosyl trehaloses and alpha-glycosyl alpha-glycosides where a solution of liquefied starch is subjected either to non-reducing saccharide-forming enzyme or non-reducing saccharide-forming enzyme and trehalose-releasing enzyme, combinations with starch-debranching enzyme and/or cyclomaltodextrin glucanotransferase improve the yields for such non-reducing saccharides to levels which are hardly attainable only with reducing-saccharide-forming enzyme and trehalose-releasing enzyme. The non-reducing saccharides and less reducing reducing saccharides containing the same commonly bear a variety of desirable properties which make them useful in a variety of compositions including food products, cosmetics and medicines.

22 Claims, 17 Drawing Sheets

NON-REDUCING SACCHARIDE AND ITS PRODUCTION AND USE

CROSS-REFERENCE TO RELATED APPLICATIONS

This application is a continuation in part of Ser. No. 08/253,171, filed Jun. 2, 1994, now U.S. Pat. No. 5,472,863.

BACKGROUND OF THE INVENTION

1. Field of the Invention

The present invention relates to non-reducing saccharides and their production and use, in particular, to non-reducing saccharides including trehalose and non-reducing saccharides bearing at their ends or within their molecules trehalose structures, a process to produce the same from starch and a composition which contains such a non-reducing saccharide or less reducing saccharide containing the same.

2. Description of the Prior Art

Trehalose (alpha,alpha-trehalose) has been known from ancient times as a non-reducing saccharide composed of glucose, and as described in *Advances in Carbohydrate Chemistry*, published by Academic Press Inc., New York, N.Y., USA, Vol.18, pp.201–225 (1963) and *Applied and Environmental Microbiology*, Vol.56, pp.3,213–3,215 (1990), its trace but extensive distribution is found in microorganisms, mushrooms and insects. Since non-reducing saccharides cause no aminocarbonyl reactions with substances bearing amino groups such as amino acids and proteins and therefore neither deteriorate nor alter them, as is the case with trehalose the saccharides have been deemed to be useful in utilizing and processing such substances with no fears of their browning and deterioration: Thus establishment of processes which would enable their industrial-scale production has been logd desired.

There have been known several processes to produce trehalose, for example, those using microorganism cells as disclosed in Japanese Patent Kokai No. 154,485/75 and those converting maltose by combination of maltose phosphorylase and trehalose phosphorylase. The former process using micro-organism cells is however inadequate for industrial-scale process because the trehalose content in microorganism cells as starting material is generally low, i.e. less than 15 w/w % (the percentages appeared hereinafter mean "w/w %" unless specified otherwise), and the extraction and purification steps for trehalose are very complicated. The latter process using maltose phosphorylase and trehalose phosphorylase has not been realized in industrial scale due to the demerits that both enzymes commonly act via glucose-1-phosphate and this hinders elevated concentrations for substrates. The yield for trehalose is low because both enzymes irreversibly act in the same reaction system, and further that such reaction system is very difficult to maintain stable and proceed smoothly.

In connection with this, *Gekkan Food Chemical* (*Monthly Food Chemical*), "Recent Aspects and Issues in Utilization and Development of Starch", August, pp.67–72 (1992) comments in the corner of "Oligosaccharides" that although trehalose would have very extensive uses, its enzymatic production using any direct saccharide-transferring or hydrolyzing reactions has been deemed to be scientifically impossible at the present time, confirming that the production of trehalose from starch as material using enzymatic reactions has been deemed to be scientifically impossible.

It is known that partial starch hydrolysates, for example, liquefied starch, dextrins and maltooligosaccharides which are all produced from starch, generally exhibit reducing powers due to the reducing end groups in their molecules. Such a partial starch hydrolysate will be designated as "reducing partial starch hydrolysate" in this specification. The reducing powers of reducing partial starch hydrolysates on dry solid basis are usually expressed by "Dextrose Equivalent" or "DE". Also it is known that reducing partial starch hydrolysates with higher DE values, which are generally small molecules, exhibit low viscosities and strong sweetening powers, as well as high reactivities to substances with amino groups such as amino acids and proteins, which cause the aminocarbonyl reaction leading to browning, unpleasant smell and deterioration.

The characteristics of reducing partial starch hydrolysates vary depending on the magnitudes of their DE and therefore the relationship between particular reducing partial starch hydrolysates and their DE values is very important. It has been however believed in the art to be impossible to obviate this relationship.

The sole method to obviate the relationship is to change reducing partial starch hydrolysates into non-reducing saccharides, for example, by converting their reducing groups into alcohol groups by high-pressure hydrogenation. This method however needs high-pressure autoclaves, safety facilities and careful control to prevent disasters, and requires large amounts of hydrogen and energy. Further the obtained saccharide alcohols differ from reducing partial starch hydrolysates in the fact that reducing partial starch hydrolysates consist of glucose moieties, while the saccharide alcohols consist of glucose and sorbitol and this may cause transient indigestion and diarrhea. Thus there has been in a great demand to establish any methods by which the reducing powers of reducing partial starch hydrolysates are decreased or even eliminated without changing glucose moieties which compose reducing starch hydrolysates.

To solve these, the present inventors disclose in Japanese Patent Application No. 349,216/93 a novel non-reducing saccharide-forming enzyme (referred to as "non-reducing saccharide-forming enzyme" hereinafter) which is capable of forming non-reducing saccharides bearing at their ends trehalose structures from one or more reducing partial starch hydrolysates with glucose polymerization degrees of 3 or higher, thus establishing non-reducing saccharides bearing at their molecular ends trehalose structures and less reducing saccharides containing the same, as well as establishing a process to produce trehalose from these saccharides using the non-reducing saccharide-forming enzyme.

It was however found later that the non-reducing saccharides obtained by this process were less in reducing power but somewhat too high in viscosity when reducing partial starch hydrolysates used as starting material were relatively large molecules, while one obtained an insufficient decrease of reducing power when reducing partial starch hydrolysates used as starting material were relatively small molecules. Also was found that production of trehalose where the non-reducing saccharides thus obtained were subjected to glucoamylase was too low in the yield from starch as material to enable industrial-scale production of trehalose. To improve these, there has been in a great demand to establish any methods which would give much smaller non-reducing saccharides from reducing partial starch hydrolysates at higher yields.

The present inventors also disclose in Japanese Patent Application No. 79,291/94 a novel trehalose-releasing enzyme (referred to as "trehalose-releasing enzyme" hereinafter) which specifically hydrolyzes the linkages between the trehalose moieties and other moieties in non-reducing saccharides with glucose polymerization degrees of 3 or higher, as well as establishing a process to produce trehalose at a relatively high yield where the non-reducing saccharide-forming enzyme and trehalose-releasing enzyme are used in combination. To produce trehalose in industrial scale, there has been however in a great expectation to establish any processes which would realize an improved yield for trehalose.

SUMMARY OF THE INVENTION

The present invention provides a process to produce from starch as low cost and consistently available material non-reducing saccharides and less reducing saccharides containing the same including relatively small non-reducing saccharides bearing at their ends trehalose structures (referred to as "alpha-glycosyl trehalose" hereinafter), non-reducing saccharides bearing at both ends in their molecule trehalose structures, in other words, those bearing within their molecules trehalose structures (referred to as "alpha-glycosyl alpha-glycoside" hereinafter) and trehalose at elevated yields, as well as to provide their use.

To solve these objects, the present inventors have energetically investigated various processes to produce non-reducing saccharides using starch as starting material. As the result, the present inventors found that the objects were attained by the process where starch-debranching enzyme and/or cyclomaltodextrin glucanotransferase is used in combination when a solution of liquefied starch is subjected either to non-reducing saccharide-forming enzyme or to non-reducing saccharide-forming enzyme and trehalose-releasing enzyme. Thus the present inventors accomplished the present invention.

More particularly, it was found that in the production of alpha-glycosyl trehaloses or less reducing saccharides containing the same where a solution of liquefied starch with a relatively low DE, desirably, DE lower than 15, is subjected to non-reducing saccharide-forming enzyme, less reducing saccharides containing non-reducing saccharides obtained by subjecting further to starch-debranching enzyme and/or cyclomaltodextrin glucanotransferase became lower in molecular weight and viscosity and more easily handleable with no substantial increases in reducing power than in case of subjecting saccharides only to non-reducing saccharide-forming enzyme. Also was found that after subjecting the less reducing saccharides to glucoamylase, the trehalose contents in their structures were extensively elevated. Further it was found that in the production of trehalose where a solution of liquefied starch with a relatively low DE, desirably, DE lower than 15, was subjected to non-reducing saccharide-forming enzyme and trehalose-releasing enzyme, the yield for trehalose was much more improved by subjecting the startch further to starch-debranching enzyme and/or cyclomaltodextrin glucanotransferase than in case of subjecting the startch only to non-reducing saccharide-forming enzyme and trehalose-releasing enzyme. The non-reducing saccharides and less reducing saccharide containing the same thus obtained are high in stability, easily handleable and therefore feasible in extended uses, for example, in a variety of compositions including food products, cosmetics and medicines.

DETAILED DESCRIPTION OF THE INVENTION

Figure 1:
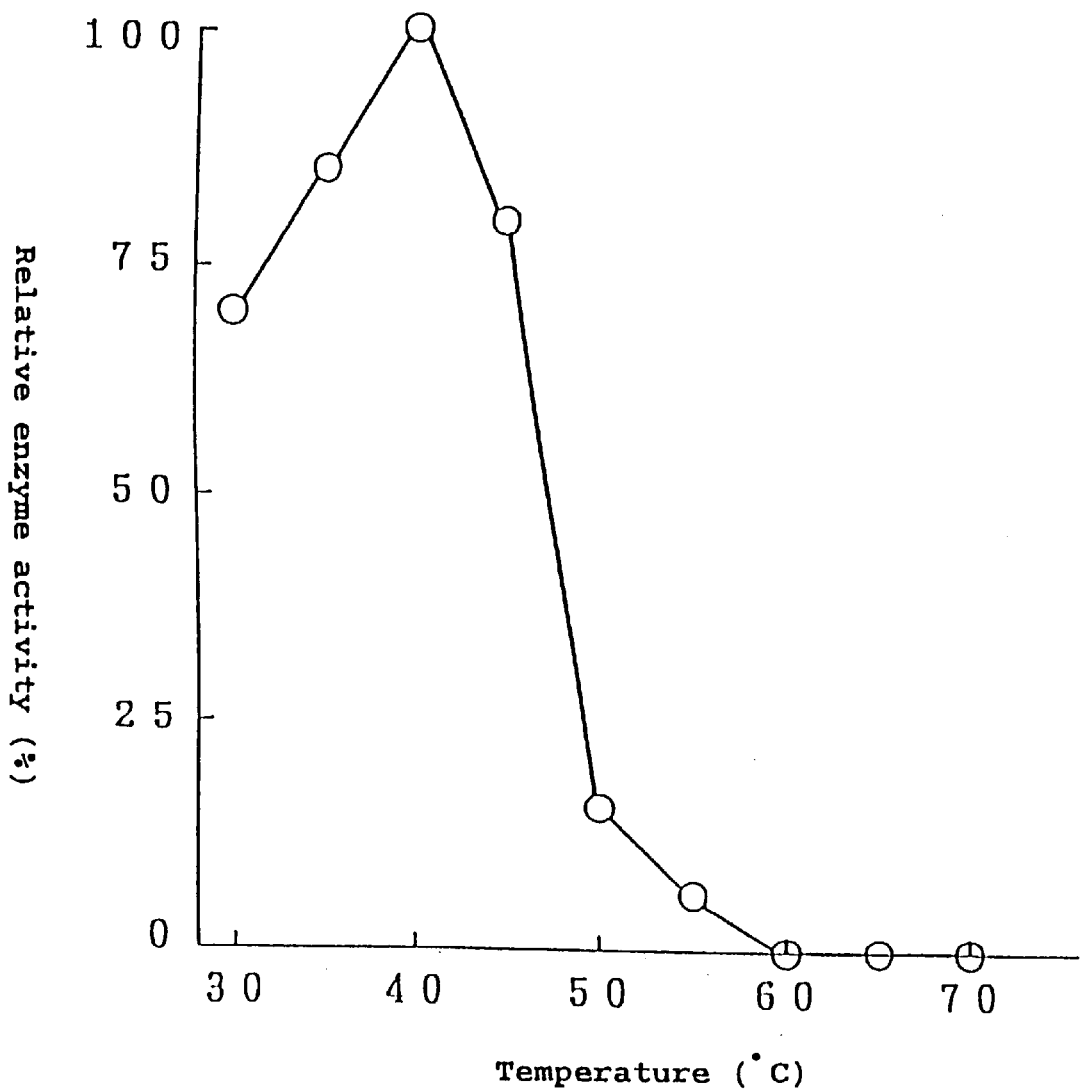
FIG. 1 shows the effect of temperature on the activity of the non-reducing saccharide-forming enzyme derived from Rhizobium species M-11.

First, the non-reducing saccharide-forming enzymes feasible in the present invention are those which are capable of forming alpha-glycosyl trehaloses from one or more reducing partial starch hydrolysates with glucose polymerization degrees of 3 or higher in solutions of starch which has been liquefied to a relatively low DE: Examples of such an enzyme are those derived from micro-organisms of the genera Rhizobium, Arthrobacter, Brevibacterium, Flabobacterium, Micrococcus, Curtobacterium, Mycobacterium and Terrabacter which are disclosed in Japan Patent Application No. 349,216/93. If necessary, heat-resistant non-reducing saccharide-forming enzymes, for example, those from the genus Sulfolobus as disclosed in Japanese Patent Application No. 166,011/94 by the same applicant, can be arbitrarily used. The trehalose-releasing enzymes are such as those which specifically hydrolyze the linkages between the trehalose moieties and the other moieties in alpha-glycosyl trehaloses which have been formed by subjecting a solution of liquefied starch to non-reducing saccharide-forming enzyme. Examples of such an enzyme are those derived from the genera Rhizobium, Arthrobacter, Brevibacterium and Micrococcus which are all disclosed in Japanese Patent Application No. 79,291/94. If necessary, heat-resistant trehalose-releasing enzymes, for example, those as disclosed in Japanese Patent Application No. 166, 126/94 by the same applicant, can be arbitrarily used. To prepare non-reducing saccharide-forming enzyme and/or trehalose-releasing enzyme, micro-organisms capable of producing either of both of the enzymes are cultivated.

Such cultivation is carried out on synthetic or natural culture media where the objective micro-organism can grow and produce non-reducing saccharide-forming enzyme and/or trehalose-releasing enzyme. The carbon sources are substances which are assimilable by such a micro-organism including saccharides, for example, glucose, fructose, lactose, sucrose, mannitol, sorbitol, sugar syrup and reducing partial starch hydrolysates, and organic acids and their salts, for example, citric acid, succinic acid and their salts. The concentration of carbon source in culture media is arbitrarily chosen depending on the types of particular carbon sources. For example, in the case of reducing partial starch hydrolysates, preferable concentrations are usually 20% or lower, preferably, 5% or lower with viewpoints of growth and proliferation of micro-organisms. Examples of nitrogen sources are inorganic salts such as ammonium salts and nitrates and organic nitrogen compounds such as urea, corn steep liquor, casein, peptone, yeast extract and meat extract. Example of minerals are calcium salts, magnesium salts, potassium salts, sodium salts, phosphates, manganese salts, zinc salts, iron salts, copper salts, molybdenum salts and cobalt salts. If necessary, amino acids and vitamins can be arbitrarily used.

Cultivation is usually carried out under aerobic conditions at 4–40° C., desirably, 20–37° C. and at pH4–10, desirably, pH5–9. In the case of micro-organisms producing heat-resistant enzymes, the temperature is usually set to 40–90° C., desirably, 50–80° C., while the pH, 2–10, desirably, 3–9. Cultivation time is set to a level where micro-organisms can proliferate, for example, 10–100 hours. There are provided no special limitations in the oxygen concentration in cultures but preferred levels are usually 0.5–20 ppm. For this purpose, one can control aeration, stir, supplement oxygen and/or elevate the pressure in fermenters. Cultivation can be carried out in batch or continuous manner.

Microorganisms are cultivated as above and the enzymes are then recovered. Enzymatic activities are found in both cells and supernatants of cultures and therefore one can recover them as crude enzyme preparation or use whole cultures intact as crude enzyme preparation. To remove cells from cultures, conventional solid/liquid separation methods are employed. For example, one can arbitrarily choose a method where cultures are subjected to centrifugal separation, another method where cultures are separated by filtration using pre-coated filters, and still another method where cultures are separated by membrane filtration using plain membranes and hollow fibers. Cell-free liquids can be used intact as crude enzyme preparation but are usually concentrated prior to use. Concentration can be carried out, for example, by ammonium sulfate precipitation method, acetone/alcohol precipitation method and membrane concentration using plain membranes and hollow fibers.

Cell-free liquids and their concentrates can be immobilized in conventional manner. For this purpose, for example, binding to ion exchanges, covalent attachment or adsorption to resins and membranes and entrapment using polymers are employed. Cells, which have been separated from cultures, are used intact as crude enzyme preparation or immobilized prior to use. For example, cells are first mixed with sodium arginate, then dropped and gelatinized in calcium chloride solution into granular form. The granules may be further treated with polyethyleneimine or glutaraldehyde. One can extract enzymes from cells and use the extract as crude enzyme liquid. For example, cells are subjected first to ultrasonic disruption, mechanical disruption using glass beads and aluminum or French press disruption for extraction of enzymes, then to centrifugal separation or membrane filtration, thus obtaining a transparent crude enzyme liquid.

Such an enzyme liquid is used intact or further purified in conventional manner prior to use. For example, a crude enzyme preparation from culture which has been subjected to salting out by ammonium sulfate and concentration is first dialyzed, then purified on anion exchange column chromatography using "DEAE TOYOPEARL", hydrophobic column chromatography using "BUTYL TOYOPEARL" and gel filtration chromatography using "TOYOPEARL HW-55", all of which are products of Tosoh Corp., Tokyo, Japan, thus obtaining an electrophoretically homogenous enzyme preparation.

The non-reducing saccharide-forming enzymes thus obtained generally bear the following physicochemical properties:

(1) Action Capable of forming alpha-glycosyl trehaloses from one or more reducing partial starch hydrolysates with glucose polymerization degrees of 3 or higher.

(2) Molecular weight About 76,000–87,000 daltons on SDS-gel electrophoresis.

(3) Isoelectric point About pI3.6–4.6 on Ampholine electrophoresis.

(4) Optimum temperature Around 35–40° C. when allowed to react at pH7.0 for 60 minutes.

(5) Optimum pH About pH6.4–7.2 when allowed to react at 40° C. for 60 minutes.

(6) Thermal stability Stable up to about 35–40° C. when incubated at pH7.0 for 60 minutes.

(7) pH Stability About pH5.5–11.0 when incubated at 25° C. for 16 hours.

Non-reducing saccharide-forming enzyme is assayed as follows: 4 ml of 25 w/v % maltopentaose as substrate in 50 mM phosphate buffer (pH7.0) is added with 1 ml enzyme liquid, allowed to react at 40° C. for 60 minutes, heated at 100° C. for 10 minutes to suspend the reaction, accurately diluted by 10-times in deionized water and determined for reducing power by the Somogyi-Nelson method. As control, an enzyme liquid which has been inactivated by heating at 100° C. for 10 minutes is treated similarly as above. One unit of the enzyme is defined as the amount of enzyme that decreases the reducing power by 1 micromole for one minute in terms of the amount of maltopentaose under the above assay conditions.

While the trehalose-releasing enzymes obtained as above generally have the following physicochemical properties:

(1) Action Capable of specifically hydrolyzing the linkages between the trehalose moieties and the other moieties in alpha-glycosyl trehaloses.

(2) Molecular weight About 57,000–68,000 daltons on SDS-gel electrophoresis.

(3) Isoelectric point About pI3.3–4.6 on Ampholine electrophoresis.

(4) Optimum temperature Around 35–45° C. when allowed to reacted at pH7.0 for 30 minutes.
(5) Optimum pH About pH6.0–7.5 when allowed to act at 40° C. for 30 minutes.
(6) Thermal stability Stable up to about 30–45° C. when incubated at pH7.0 for 60 minutes.
(7) pH Stability About pH5.0–10.0 when incubated at 25° C. for 16 hours.

Trehalose-releasing enzyme is assayed as follows: 4 ml of 1.25 w/v % maltotriosyl trehalose or alpha-maltotetraosyl alpha-D-glucoside as substrate in 50 mM phosphate buffer (pH7.0) is added with 1 ml of enzyme liquid, allowed to react at 40° C. for 30 minutes, added with Somogyi's copper liquid to suspend the reaction and assayed for reducing power by the Somogyi-Nelson method. As control, an enzyme liquid which has been inactivated by heating at 100° C. for 10 minutes is treated similarly as above. One unit of the enzyme is defined as the amount of the enzyme that increases reducing power by one micromole for 1 minute in terms of the amount of glucose under the above assay conditions.

The starch-debranching enzymes feasible for use in the present invention are those which act on a solution of liquefied starch with a relatively low DE, desirably, DE lower than 15, and hydrolyze branches in the starch and conventional pullulanase and isoamylase. Commercially-available enzyme preparations can be favorably used. While the cyclomaltodextrin glucanotransferase as referred to the present invention is an enzyme which acts in a solution of liquefied starch with a relatively low DE, desirably, DE lower than 15, and arises saccharide-transfer reaction and disproportionation in starch saccharides and those derived from conventional micro-organisms of the genera Bacillus and Klebsiella and commercially-available enzyme preparations can be favorably used.

Other amylases, in particular, those which act on a solution of liquefied starch with a relatively low DE to form oligosaccharides with glucose polymerization degrees of 3 or more as predominant products can be favorably used along with the above mentioned starch-debranching enzyme and/or cyclomaltodextrin glucanotransferase: Examples of such an amylase include alpha-amylase, maltotriose-forming amylase, maltotetraose-forming amylase, maltopentaose-forming amylase, maltohexaose-forming amylase and maltoheptaose-forming amylase.

Terrestrial starches such as cornstarch, rice starch and wheat starch and subterranean starches such as potato starch, sweet potato starch and tapioca starch are all feasible in the present invention. To liquefy such a starch, the starch is usually suspended in water, desirably, to 10% or higher, more desirably, to about 20–50%, heated and subjected to mechanical, enzymatic or acid liquefaction. The liquefaction degree is relatively low, in particular, lower than 15, preferably, lower than 10 in terms of DE. In case of liquefying with acids, for example, at first, hydrochloric acid, phosphoric acid or oxalic acid is used, then calcium carbonate, calcium oxide or sodium carbonate is used for neutralization to prescribed pH. In case of liquefying with enzymes, alpha-amylases, in particular, heat-resistant liquefying alpha-amylases are preferred.

To subject the solution of liquefied starch thus obtained either to non-reducing saccharide-forming enzyme and starch-debranching enzyme and/or cyclomaltodextrin glucanotransferase or to non-reducing saccharide-forming enzyme, trehalose-releasing enzyme and starch-debranching enzyme and/or cyclomaltodextrin glucanotransferase, pH and temperature are set to levels where these enzymes are active, in particular, pH4–10, desirably, pH5–8 and a temperature of about 10–80° C., desirably, about 30–70° C. There are however no limitations in the order of using the enzymes and they are successively or simultaneously used.

The amounts of enzymes to be used are arbitrarily chosen depending on reaction conditions including reaction time: Usually, against liquefied starch in solution, non-reducing saccharide-forming enzyme and trehalose-releasing enzyme are used in about 0.01–100 units/g solid; starch-debranching enzyme, about 1–10,000 units/g solid; and cyclomaltodextrin glucanotransferase, about 0.05–500 units/g solid. The less reducing saccharides thus obtained which contain non-reducing saccharides are characterized in that they contain large amounts of relatively small alpha-glycosyl trehaloses or alpha-glycosyl alpha-glycosides or trehalose because starch-debranching enzyme and/or cyclomaltodextrin glucanotransferase acts on a solution of liquefied starch together with either non-reducing saccharide-forming enzyme or non-reducing saccharide-forming enzyme and trehalose-releasing enzyme. The wording "alpha-glycosyl alpha-glycoside" includes alpha-D-oligoglucosyl alpha-D-oligoglucosides which are disclosed in Japanese Patent Application No. 54,377/94 by the present applicant.

The reaction mixtures are subjected to filtration and centrifugation in conventional manner to remove insoluble substances, decolored with activated carbon, deionized, purified with ion exchanges of H- and OH-forms and concentrated into syrup products. The products can be arbitrarily dried into powder. Non-reducing saccharides of the possible highest purity can be easily obtained by further purifying the syrup products with one or more methods, for example, fractionation using column chromatographies such as ion exchange column chromatography, activated carbon column chromatography and silica gel column chromatography, fractional precipitation using organic solvents such as alcohol and acetone, separation using membranes with appropriate separating abilities, fermentation treatment by yeast and alkali treatment so as to remove or to decompose the remaining reducing saccharides, if necessary.

It is favorable in industrial-scale production to use ion exchange column chromatography on strongly-acidic cation exchanges, for example, those disclosed in Japanese Patent Kokai Nos.23,799/83 and 72,598/83 so as to remove contaminant saccharides and also to increase the contents for objective non-reducing saccharides. In this case, one can arbitrarily choose from among fixed bed method, moving bed method and simulated-moving bed method.

If necessary, one can degrade non-reducing saccharides bearing trehalose structures within their molecules or less reducing saccharides containing the same with alphaglucosidases or amylases, for example, alpha-amylase, betaamylase and glucoamylase so as to control their sweetening and reducing powers and/or to decrease their viscosities and, alternatively, hydrogenate the remaining reducing saccharides into saccharide alcohols so as to eliminate their reducing powers.

Especially, trehalose can be easily produced by subjecting non-reducing saccharides bearing trehalose structures within their molecules or less reducing saccharides containing the same to glucoamylase or alpha-glucosidase. Non-reducing saccharide or less reducing saccharide is subjected to glucoamylase or alpha-glucosidase into a solution of a mixture of trehalose and glucose which is then subjected to the above mentioned purification methods, for example, ion exchange column chromatography so as to remove glucose and also to recover trehalose-rich fractions. The fractions can be purified and concentrated into a syrup product which may be further concentrated to a supersaturated state and crystallized into crystalline trehalose hydrate or anhydrous crystalline trehalose.

To produce crystalline trehalose hydrate, for example, a high-trehalose content liquid, purity of about 60% or higher, concentration of about 65–90%, is placed in a crystallizer and gradually cooled at 95° C. or lower, desirably, at 10–90° C., if necessary, in the presence of 0.1–20% seed crystals to obtain a massecuite which contains crystalline trehalose hydrate. In this case, one can favorably employ a continuous crystallization method where trehalose is crystallized while concentrating under reduced pressure. Examples of methods which yield crystalline trehalose hydrate or saccharide mixture solid containing the same from such a massecuite include conventional crystal separation method, block pulverization method, fluidized-bed granulation method and spray drying method.

The crystal separation method is suitable to produce crystalline trehalose hydrate with an elevated purity, where massecuites are usually fed to a basket-type centrifuge where they are separated into crystalline trehalose hydrate and mother liquor, after which the former crystals are sprayed with a minimum amount of chilled water for washing. In the spray drying method, massecuites, concentration of 70–85%, crystallizing ratio up to 20–60%, are usually sprayed through a nozzle combined with a high pressure pump, dried within a stream of hot air at a temperature where crystalline powder does not melt, for example, 60–100° C. and aged in a stream of hot air, temperature of 30–60° C., for about 1–20 hours, thus easily obtaining non- or less-hygroscopic crystalline mixture solids. In the block pulverization method, massecuites with moisture contents of 10–20%, crystallizing ratio up to 10–60%, are usually crystallized by allowing to stand for about 0.1–3 days into solids in block form which are then pulverized and dried by cutting or scraping, thus obtaining non- or less-hygroscopic crystalline mixture solids.

While to produce anhydrous crystalline trehalose, crystalline trehalose hydrate is converted by drying and, alternatively, a concentrated high-trehalose content liquid, moisture content less than 10%, is usually placed in a crystallizer and stirred at 50–160° C., desirably, 80–140° C., in the presence of seed crystals to obtain a massecuite which is then crystallized and pulverized, for example, by block pulverization method, fluidized-bed granulation method and spray drying method under relatively hot and dried conditions.

The non-reducing saccharides and less reducing saccharide containing the same both according to the present invention thus obtained neither cause browning and unpleasant smell nor damage in other substances, in particular, those with amino acids, such as amino acids, oligopeptides and proteins when mixed or processed therewith because the saccharides are stable due to their decreased reducing powers. Further the saccharides are low in reducing power and viscosity and those with low averaged glucose polymerization degrees commonly exhibit a high-quality and mild sweetness.

Further the saccharides are digested, absorbed and utilized as sources of calories when orally ingested because they are degraded by amylases, in particular, pancreas alpha-amylase, into small non-reducing oligosaccharides and small maltooligosaccharides which are readily degraded by alpha-glucosidase and small intestine enzymes to form glucose together with trehalose which is then degraded into glucose by trehalase. Still further the saccharides are feasible as sweetners less likely to cause caries because they are hardly fermented by dental caries-causative microorganisms. Still further the saccharides bear other desirable properties such as osmosis controlling ability, shape imparting ability, gloss imparting ability, moisture retaining ability, viscosity, ability of preventing crystallization of other saccharides, decreased fermentability and ability of preventing retrogradation of gelatinized starch.

The trehalose according to the present invention can be favorably used for energy supplementation to living bodies because it is readily metabolized and utilized with no fears of toxicity or side effect when parenterally used in intubation feeding or infusion form. Crystalline high-trehalose content products can be favorably used as coating agents for tablets in combination with binders such as pullulan, hydroxyethyl starch and polyvinyl pyrrolidone because trehalose acts as a stable sweetener.

Further the trehalose of the present invention can be used as a moisture-retaining agent, filler and viscosity-imparting agent in cosmetic cream, hair rinse, milky lotion and face lotion: In this case, when trehalose is used along with other moisture retaining agents, for example, propylene glycol, 1,3-butylene glycol, glycerin, sorbitol and polyoxyethylene oleil alcohol and vitamins such as alpha-glucosyl-L-ascorbic acid and enzyme-treated rutin, one can favorably obtain cosmetics with superior moisture retainabilities which include the ability to prevent spots and freckles due to ultraviolet radiation and also to whiten the skin.

Anhydrous crystalline trehalose can be favorably used as a desiccant for hydrous substances such as food products, cosmetics, medicines and materials and intermediates thereof to facilitate the production of stable and high-quality solid products including powders, granules and tablets.

Thus the non-reducing saccharide and less reducing saccharide containing the same both according to the present invention can be favorably used as sweetener, taste improving agent, quality improving agent, stabilizer, shape imparting agent and desiccant in a variety of compositions including food products, tobacco, cigarette, feeds, cosmetics and medicines.

The non-reducing saccharide and less reducing saccharide containing the same both according to the present invention can be used intact as a seasoning for sweetening. If necessary, they can be mixed with an appropriate amount of one or more other sweeteners and/or fillers, for example, starch syrup powder, glucose, maltose, sucrose, isomerized sugar, honey, maple sugar, isomaltooligosaccharide, galactooligosaccharide, fructooligosaccharide, lactosucrose, sorbitol, maltitol, lactitol, dihydrochalcone, stevioside, alpha-glycosyl stevioside, rhebaudioside, glycyrrhizin, L-aspartyl-L-phenylalanine methyl ester, saccharin, glycine, dextrin, starch and lactose, prior to use.

The non-reducing saccharides and less reducing saccharides containing the same both according the present invention can be shaped intact or, if necessary, along with a filler, vehicle and binder into desired shapes, for example, granule, globe, rod, plate, cube and tablet.

The non-reducing saccharides and less reducing saccharides containing the same both according to the present invention can be favorably used to sweeten and/or to improve the tastes and qualities in food products in general because they superiorly harmonize with a variety of substances with other types of tastes such as sour, salty, astringent, delicious and bitter tastes.

For example, they can be favorably used, for example, in a variety of seasonings such as amino acids, peptides, soy sauce, powdered soy sauce, miso, powdered miso, "moromi", "hishio", "furikake", mayonnaise, dressing, vinegar, "sanbaizu", powdered vinegar for "sushi", "chuka-no-moto", "tentsuyu", "mentsuyu", sauce, catsup, "yakiniku-no-tare", curry roux, stew stock, soup stock, "dashi-no-moto", nucleic acid seasoning, mixed seasoning, "mirin", "shin-mirin", table sugar and coffee sugar.

Further they can be favorably used to sweeten and/or to improve the tastes and qualities, for example, in a variety of Japanese-style confectioneries such as "senbei", "arare", "okoshi", "ame", "manju", "uiro", bean pastes, "yokan", "mizuyokan", "kingyoku", jelly, castella and "amedama": Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as preserved fruits and "kori-mitsu": pastes such as flour paste, peanut paste, fruit paste and spread; processed fruits and vegetables such as jam, marmalade, preserved fruits and vegetables and "toka": pickles and pickled products such as "fukuzin-zuke", "bettara-zuke", "senmai-zuke" and "rakkyo-zuke"; stocks for pickled products such as "takuan-zuke-no-moto" and "hakusai-zuke-no-moto"; meat products such as ham and sausage; fish meat products such as fish meat ham, fish meat sausage, "kamaboko", "chikuwa" and "tenpura"; relish such as "uni-no-shiokara", "ika-no-shiokara", "su-konbu", "saki-surume" and "fugu-no-mirin-boshi"; "tsukudani" such as those of seaweed, "sansai", "surume", small fish and shell-fish; daily dishes such as "nimame", potato salad and "konbu-maki"; milk product such as yoghurt and cheese; canned and bottled products such as those of fish meat, meat, fruits and vegetables; alcoholic beverages such as sake, synthetic sake, liquors and Western-style alcoholic beverages; soft drinks such as coffee, tea, cocoa, juice, carbonated drink, lactic acid drink and drink containing lactic acid bacteria; convenience foods such as pudding mix, hot cake mix, "sokuseki-shiruko" and convenience soup; and other types of food products such as infants' foods, treatment foods, bottled beverages, peptide foods, chilled foods and dried foods.

Still further the saccharides can be favorably used as a sweetener, taste improving agent, taste masking agent, quality improving agent and stabilizer to improve taste qualities of feeds such as those for domestic animals, poultry, honey bees, silk worm and fish. They are also favorably used in a variety of compositions in solid, paste or liquid form such as tobacco, cigarette, cosmetics and medicines including dentifrice, lip stick, lip cream, internal medicine, tablet, troche, cod liver oil drops, oral refreshing agent and gargle.

The uses as quality improving or stabilizer include those for a variety of bioactive substances and health foods and medicines containing the same whose effective ingredients and activities are susceptible to inactivation. Example of such a bioactive substance are lymphokines such as interferon-alpha, interferon-beta, interferon-gamma, tumor necrosis factor-alpha, tumor necrosis factor-beta, macrophage migration inhibitory factor, colony stimulating factor, transfer factor and interleukin 2; hormones such as insulin, growth hormone, prolactine, erythropoietin and follicle stimulating hormone; biological preparations such as BCG vaccine, Japanese encephalitis virus vaccine, measles vaccine, poliomyelitis vaccine, smallpox vaccine, tetanus toxoid, Trimeresurus antitoxin and human immunoglobulin; antibiotics such as penicillin, erythromycin, chroramphenicol, tetracycline, streptomycin and kanamycin sulfate; vitamins such as thiamin, riboflavin, L-ascorbic acid, cod liver oil, carotenoid, ergosterol and tocopherol; enzymes such as lipase, elastase, urokinase, protease, betaamylase, isoamylase, glucanase and lactase; extracts such as those of ginseng, snapping turtle, chlorella, aloe and propolis; live micro-organisms such as live virus, lactic acid bacteria and yeast; and other type of bioactive substances including royal jelly. Thus one can easily produce stable and high-quality health foods and medicines in liquid, paste or solid form without loosing their activities or effective ingredients.

To incorporate in such a composition the non-reducing saccharide and less reducing saccharide containing the same, the saccharides are incorporated by conventional methods, for example, mixing, dissolving, melting, soaking, permeating, spreading, applying, coating, spraying, injecting, crystallizing and solidifying prior to completion of their processings. The amounts to be incorporated are usually 0.1% or more, desirably, 1% or more.

The present invention will be more concretely explained with reference to several Experiments.

At first non-reducing saccharide-forming enzymes from novel micro-organisms Rhizobium species M-11 and Arthrobacter species Q36, then those from conventional micro-organisms will be explained.

Experiment 1

Production of non-reducing saccharide-forming enzyme from Rhizobium species M-11

A liquid culture medium consisting of 2.0 w/v % maltose, 0.5 w/v % pepton, 0.1 w/v % yeast extract, 0.1 w/v % disodium hydrogen phosphate, 0.1 w/v % potassium dihydrogen phosphate and water was adjusted to pH7.0. About 100 ml aliquots of the culture medium were distributed in 500 ml flasks, autoclaved at 120° C. for 20 minutes for sterilization, cooled, inoculated with a seed culture of Rhizobium species M-11 (FERM BP-4130) and cultivated at 27° C. and 130 rpm for 24 hours to obtain a seed culture.

About 20 liters of the same culture medium as described above was placed in 30 liter fermenter, sterilized, cooled to 30° C., inoculated with 1 w/v % seed culture and cultivated for about 24 hours under aeration and agitation conditions while retaining at 30° C. and pH6.0–8.0. The enzymatic activity in the culture was about 1.5 units/ml. A portion of the culture was sampled and centrifugally separated into cells and supernatant and the cells were then suspended in 50 mM phosphate buffer (pH7.0) to give the same volume as that of the sampled culture, followed by determining the enzymatic activities in the cell suspension and supernatant, revealing that about 0.6 units/ml of enzyme activity was found in the cell suspension, while about 0.9 units/ml, in the supernatant.

Experiment 2

Purification of enzyme

The culture, about 18 liters, obtained in Experiment 1 was subjected to "MINI LABO", a super high-pressure cell disrupter commercialized by Dainippon Pharmaceutical Co., Ltd., Tokyo, Japan, to disrupt the cells. The resultant was centrifuged at 10,000 rpm for 30 minutes to obtain about 16 liters of a supernatant. The supernatant was added with ammonium sulfate to give a saturation degree of 0.2, allowed to standing at 4° C. for 1 hour and centrifuged, followed by recovering the supernatant.

The supernatant was further added with ammonium sulfate to give a saturation degree of 0.6, allowed to standing at 4° C. for 24 hours and centrifuged to obtain the sediment. The sediment was dissolved in 10 mM phosphate buffer (pH7.0), dialyzed against a fresh preparation of the same buffer for 24 hours and centrifuged to remove insoluble substances. The dialyzed solution, about 360 ml, was divided into two portions which were then separately applied to ion exchange chromatography on 300 ml "DEAE TOYOPEARL".

The objective enzyme, which had been adsorbed on "DEAE TOYOPEARL", was eluted therefrom with a fresh preparation of the same buffer but additionally containing sodium chloride. The enzymatically active fractions thus obtained were dialyzed against a fresh preparation of the same buffer but additionally containing 2M ammonium sulfate and centrifuged to remove insoluble substances, after which the obtained supernatant was subjected to a hydrophobic column chromatography on 300 ml "BUTYL TOYOPEARL 650". The enzyme which had been adsorbed in the column was eluted therefrom under a linear gradient decreasing from 2M to 0M for ammonium sulfate, followed by recoverying the enzymatically active fractions. The fractions were applied to gel filtration chromatography on 300 ml "TOYO-PEARL HW-55" and the enzymatically active fractions were recovered. The enzymatic activities, specific activities and yields in respective purification stages were as shown in Table 1.

In the purification stages in Table 1, the purified enzyme preparation obtained as eluate of gel filtration was determined on polyacrylamide gel electrophoresis, gel concentration of 7.5% resulting in a single band of protein which confirmed that the obtained enzyme preparation was electrophoretically homogenous and high in purity.

TABLE 1

| Purification stage | Enzymatic activity (units) | Specific activity (units/mg protein) | Yield (%) |
| --- | --- | --- | --- |
| Intact culture | 26,800 | — | 100 |
| Supernatant of disrupted culture | 20,300 | 0.10 | 76 |
| Liquid immediately after salting out by ammonium sulfate | 16,100 | 0.32 | 60 |
| Eluate of ion exchange column chromatography | 11,300 | 5.5 | 42 |
| Eluate of hydrophobic column chromatography | 5,730 | 98 | 21 |
| Eluate of gel filtration | 3,890 | 195 | 15 |

Experiment 3
Properties of enzyme

The purified enzyme preparation obtained in Experiment 2 was subjected to SDS-polyacrylamide gel electrophoresis, gel concentration of 10%, and determined for molecular weight by comparing with those of the molecular weight markers commercialized by Japan Bio-Rad Laboratories, Tokyo, Japan, which had been electrophoresed on the same gel, revealing that the molecular weight of the enzyme was about 77,000–87,000 daltons.

The purified enzyme preparation was electrophoresed on polyacrylamide gel using 2% Ampholine and then measured for pH levels, revealing that the isoelectric point of the enzyme was about 3.6–4.6.

Figure 2:
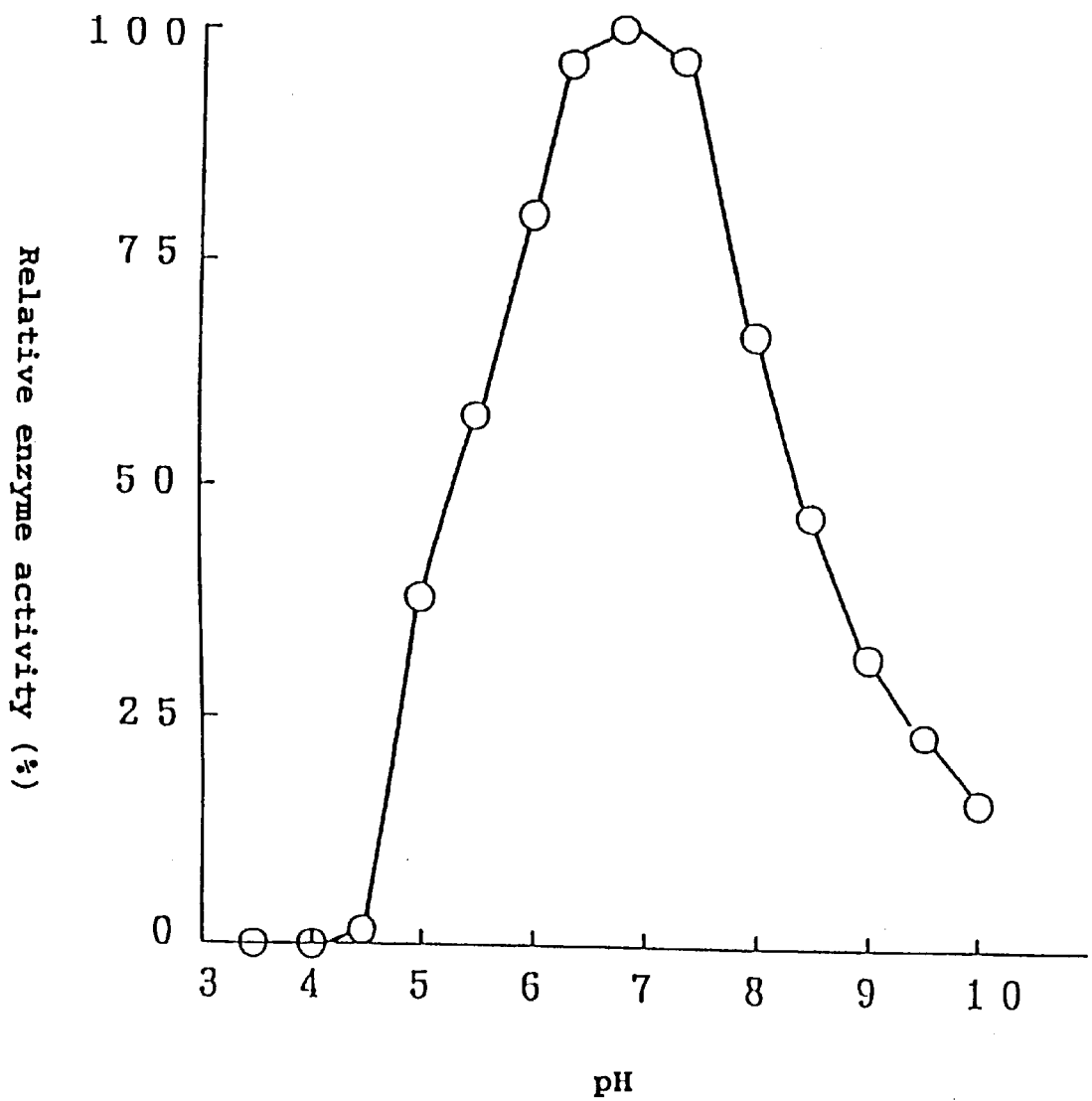
FIG. 2 shows the effect of pH on the activity of the non-reducing saccharide-forming enzyme derived from Rhizobium species M-11.
Figure 3:
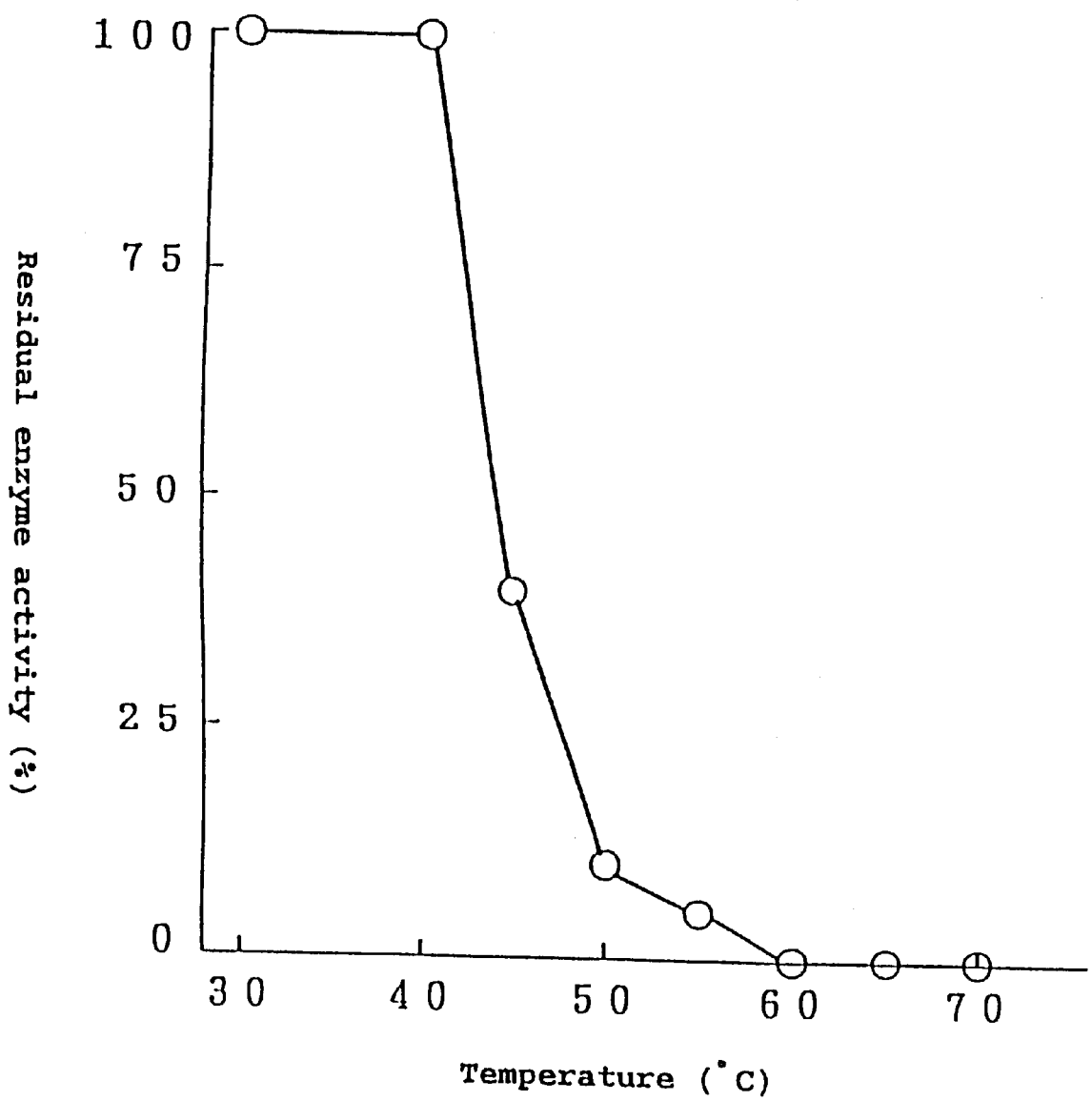
FIG. 3 shows the thermal stability of the non-reducing saccharide-forming enzyme derived from Rhizobium species M-11.
Figure 4:
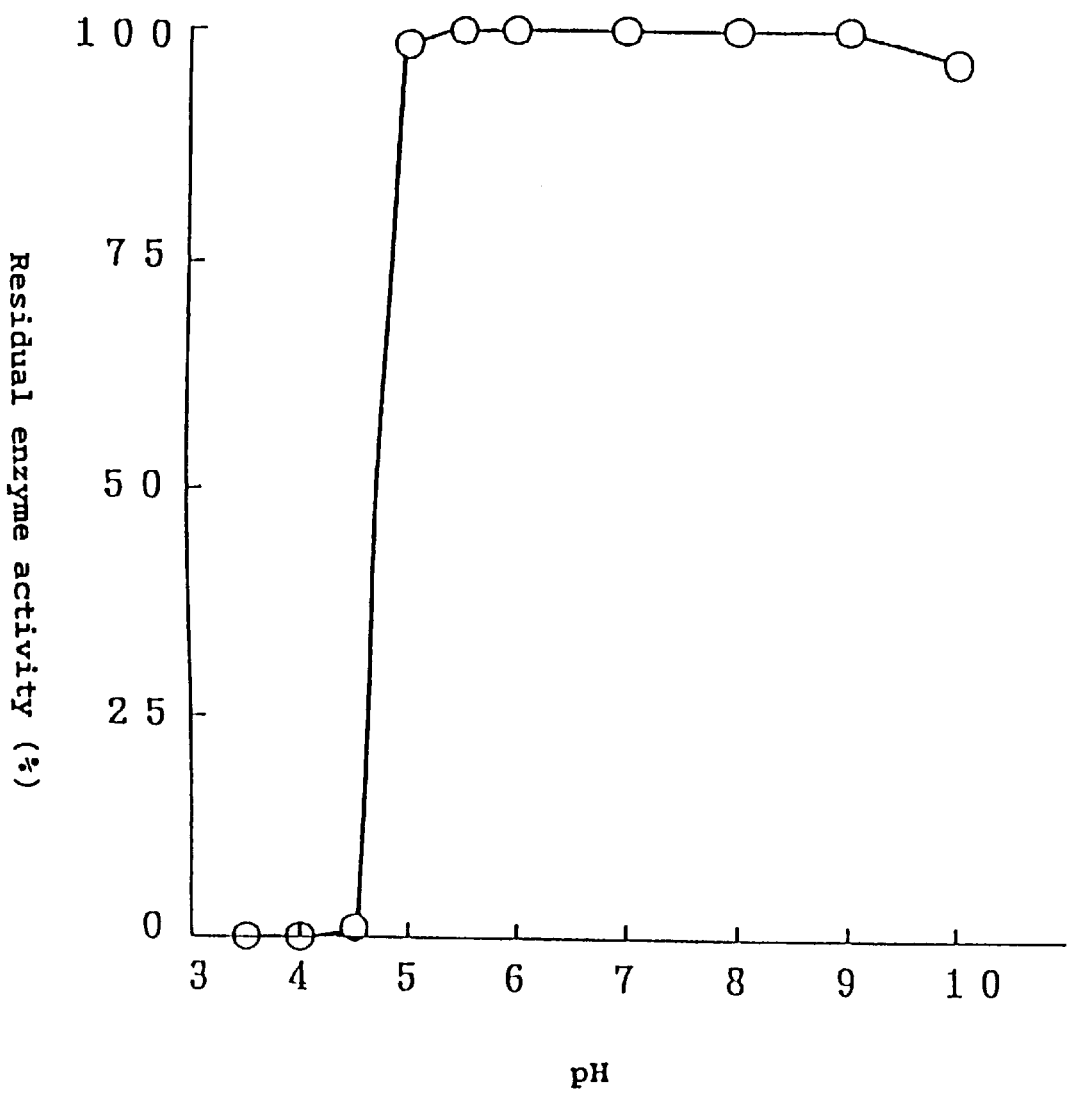
FIG. 4 shows the pH stability of the non-reducing saccharide-forming enzyme derived from Rhizobium species M-11.

Effects of temperature and pH on the activity of the enzyme were investigated in accordance with the assay method. The results were as shown in FIG. 1 for the effect of temperature and in FIG. 2 for the effect of pH. The optimum temperature of the enzyme was around 40° C. when allowed to react at pH7.0 for 60 minutes, while the optimum pH, about 7.0 when allowed to react at 40° C. for 60 minutes. The thermal stability of the enzyme was determined by incubating the enzyme in 50 mM phosphate buffer (pH7.0) at different temperatures for 60 minutes, cooling with water and assaying the residual activities. While the pH stability was determined by incubating at 25° C. for 16 hours in 50 mM phosphate buffer with different pH levels, adjusting to pH7 and assaying the residual enzyme activities. Respective results were as shown in FIG. 3 for the thermal stability and in FIG. 4 for the pH stability. The thermal stability was up to about 40° C., while the pH stability, about pH6–9.

Experiment 4
Preparation of non-reducing saccharides

20% Aqueous solutions of glucose, maltose, maltotriose, maltotetraose, maltopentaose, maltohexaose or maltoheptaose as substrate were prepared, added with 2 units/g substrate solid of the purified enzyme obtained in Experiment 2, allowed to react at 40° C. and pH7.0 for 48 hours, deionized and analyzed for reaction products on high-performance liquid chromatography using "WAKO BEADS WB-T-330", a product of Wako Pure Chemical Industries, Ltd., Osaka, Japan. The high-performance liquid chromatography was conducted at ambient temperature, where water as eluent was flowed at a rate of 0.5 ml/min and "Model RI-8012", a differential reflactometer commercialized by Tosoh Corp., Tokyo, Japan, was used for analysis. The results were as shown in Table 2.

As evident from the results in Table 2, the reaction products consisted of the residual substrates and newly formed saccharides PI, PII, PIII, PIV and PV and no other saccharides were detected. The yield for saccharide PI, glucose polymerization degree of 3, was relatively low, while very high yields were marked for saccharides PII, PIII, PIV and PV, glucose polymerization degrees of 4 or higher, i.e. 85% or higher. No saccharides were newly formed from glucose and maltose.

TABLE 2

| Substrate | Reaction product | Elution time on HPLC (min) | Composition (%) |
| --- | --- | --- | --- |
| Glucose | Glucose | 33.4 | 100.0 |
| Maltose | Maltose | 28.5 | 100.0 |
| Maltotriose | PI | 23.3 | 35.0 |
|  | Maltotriose | 25.9 | 65.0 |
| Maltotetraose | PII | 21.6 | 85.6 |
|  | Maltotetraose | 24.1 | 14.4 |
| Maltopentaose | PIII | 19.7 | 92.7 |
|  | Maltopentaose | 22.6 | 7.3 |
| Maltohexaose | PIV | 18.7 | 93.5 |
|  | Maltohexaose | 21.4 | 6.5 |
| Maltoheptaose | PV | 17.8 | 93.4 |
|  | Maltoheptaose | 21.0 | 6.6 |

Note: In the Table, PI, PII, PIII, PIV and PV represent newly formed saccharides from maltotriose, maltotetraose, maltopentaose, maltohexaose and maltoheptaose as substrate respectively.

In order to purify the newly formed saccharides from respective reaction products, the reaction products were decolored, deionized, concentrated and subjected to column fractionation on "XT-1016", a strongly-acidic cation exchange of sodium form, crosslinkage degree of 4%, commercialized by Tokyo Organic Chemical Industries, Ltd., Tokyo, Japan. The resin was packed in three jacketed-stainless steel columns, inner diameter of 2.0 cm, length of 1 m, and the columns were cascaded, added with 5 v/v % reaction product against the resin while retaining the temperature inside the columns at 55° C. and passed with 55° C. water at SV0.13 for fractionation, followed by recovering high-purity fractions with the contents for the newly formed saccharides of 97% or higher. The fractions were lyophilized into respective high-purity saccharide preparations. The yields from respective substrates on dry solid basis were about 9% for saccharide PI, about 65% for saccharide PII, about 82% for saccharide PIII, about 80% for saccharide PIV and about 77% for saccharide PV. The purities were 97.5% for saccharide PI, 98.6% for saccharide PII, 99.5% for saccharide PIII, 98.4% for saccharide PIV and 98.4% for saccharide PV.

The high-purity preparations of the newly formed saccharides were determined for reducing power by the Somogyi-Nelson method and represented in terms of DE. The results were as shown in Table 3.

As evident from the results in Table 3, there were detected trace reducing powers in each preparations. The trace reducing powers would be due to the possible residual reducing maltooligosaccharides from the substrates which might be present in the preparations and all the newly formed saccharides would be substantially non-reducing.

TABLE 3

| Saccharide preparation | Purity (%) | DE |
|---|---|---|
| PI | 97.5 | 0.83 |
| PII | 98.6 | 0.35 |
| PIII | 99.5 | 0.10 |
| PIV | 98.4 | 0.27 |
| PV | 98.4 | 0.23 |

Experiment 5
Maillard reaction

Solutions of 10% saccharide preparation PI, PII, PIII, PIV or PV prepared in Experiment 4 and 1% glycine in 50 mM phosphate buffer (pH7.0) were incubated at 100° C. for 90 minuets, cooled and determined in 1 cm cuvette for absorbance at 480 nm. As control, maltotriose, maltotetraose, maltopentaose, maltohexaose and maltoheptaose which were used as the starting materials were treated similarly as above and determined for absorbance at 480 nm. The results were as shown in Table 4.

TABLE 4

| Saccharide preparation | Coloration degree at 480 nm | Remarks |
|---|---|---|
| PI | 0.027 | Present invention |
| PII | 0.018 | Present invention |
| PIII | 0.012 | Present invention |
| PIII | 0.016 | Present invention |
| PIV | 0.015 | Present invention |
| Maltotriose | 0.623 | Control |
| Maltotetraose | 0.475 | Control |
| Maltopentaose | 0.369 | Control |
| Maltohexaose | 0.318 | Control |
| Maltoheptaose | 0.271 | Control |

As evident from the results in Table 4, the preparations of the newly formed saccharides PI, PII, PIII, PIV and PV marked very low coloration degrees by Maillard reaction which were up to only 3–6% of those for maltooligosaccharides as material, confirming that the newly formed saccharides formed by the novel enzyme according to the present invention hardly caused Maillard reaction.

Experiment 6
Enzymatic hydrolysis by glucoamylase

Fifty milligrams of the non-reducing saccharide preparation PI, PII, PIII, PIV or PV prepared in Experiment 4 was dissolved in 1 ml of 50 mM acetate buffer (pH4.5), added with one unit of the glucoamylase commercialized by Seikagaku Corp., Tokyo, Japan, incubated at 40° C. for 6 hours for enzymatic hydrolysis and analyzed for degradation products on high-performance liquid chromatography, thus detecting glucose and trehalose as sole products. The noted glucose contents, trehalose contents and their molar ratios were as shown in in Table 5.

As evident from the results in Table 5, non-reducing saccharide PI was degraded by glucoamylase into one glucose molecule and one trehalose molecule; non-reducing saccharide PII, two glucose molecules and one trehalose molecule; non-reducing saccharide PIII, three glucose molecules and one trehalose molecule; non-reducing saccharide PIV, four glucose molecules and one trehalose molecule; and non-reducing saccharide PV, five glucose molecules and one trehalose molecule.

TABLE 5

| Saccharide Preparation | Glucose (%) | Trehalose (%) | Molar ratio (glucose/trehalose) |
|---|---|---|---|
| PI | 36.2 | 63.8 | 1.07 |
| PII | 52.0 | 48.0 | 2.06 |
| PIII | 61.4 | 38.6 | 3.02 |
| PIV | 68.3 | 31.7 | 4.09 |
| PV | 72.9 | 27.1 | 5.11 |

Considering the reaction characteristics of glucoamylase, these saccharides very likely bear structures where glucose molecule(s) is bound to trehalose molecule via alpha1,4 or alpha-1,6 linkage: Saccharide PI is a non-reducing saccharide with a glucose polymerization degree of 3 where one glucose molecule is bound to one trehalose molecule; saccharide PII, another non-reducing saccharide with a glucose polymerization degree of 4 where two glucose molecules are bound to one trehalose molecule; saccharide PIII, still another non-reducing saccharide with a glucose polymerization degree of 5 where three glucose molecules are bound to one trehalose molecule; saccharide PIV, still another non-reducing saccharide with a glucose polymerization degree of 6 where four glucose molecules are bound to one trehalose molecule; and saccharide PV, still another non-reducing saccharide with a polymerization degree of 7 where five glucose molecules are bound to one trehalose molecule. After subjecting to beta-amylase similarly as above, non-reducing saccharides PI and PII were not degraded; non-reducing saccharides PIII was degraded into one maltose molecule and one saccharide PI molecule; non-reducing saccharide PIV, into one maltose molecules and one saccharide PII molecule; and non-reducing saccharide PV, into two maltose molecules and one saccharide PI molecule.

The above evidence suggests that the reaction by the non-reducing saccharide-forming enzyme according to the present invention would be a type of intramolecular conversion reaction which accompanies neither degradation nor polymerization of substrates, in other words, accompanies no changes in glucose polymerization degrees, as well as suggesting that the non-reducing saccharides PI, PII, PIII, PIV and PV which are formed by the non-reducing saccharide-forming enzyme would be alpha-glucosyl trehalose, alpha-maltosyl trehalose, alpha-maltotriosyl trehalose, alpha-maltotetraosyl trehalose and alpha-maltopentaosyl trehalose respectively which can be commonly represented by the general formula "alpha-glycosyl trehalose (Gn-T where G, n and T mean glucose residue, an integer of 1 or more and alpha-trehalose respectively)".

Experiment 7

Degradation by other enzymes

The non-reducing saccharide preparations PI, PII, PIII, PIV and PV as substrates prepared in Experiment 4 were subjected to pig pancreas alpha-amylase, rice alpha-glucosidase and acetone-pulverized rat small intestine enzyme, all of which were products of Sigma Chemical Co., St Louis, Mo., USA, and the degradation products were analyzed on high-performance liquid chromatography for saccharide composition. The reaction by alpha-amylase was carried out by dissolving 10 mg of either substrate in 1 ml of 50 mM phosphate buffer (pH6.9), adding thereto one unit of alpha-amylase and incubating at 37° C. for 18 hours. The reaction by alpha-glucosidase was conducted similarly as in the case of alpha-amylase except that 50 mM acetate buffer (pH4.0) was used. In the case of acetone-pulverized rat small intestine enzyme, the reaction was conducted similarly as in the case of alpha-amylase except that 50 mM maleic acid buffer (pH6.0) was used. The saccharide compositions in the degradation products by alpha-amylase, alpha-glucosidase and acetone-pulverized rat small intestine enzyme were as shown in Tables 6, 7 and 8 respectively.

TABLE 6

| Saccharide preparation | Composition in degradation product by alpha-amylase (%) | | | | |
|---|---|---|---|---|---|
| | PI | PII | G3 | G2 | G1 |
| PI | 97.3 | 0 | 2.3 | 0.4 | 0 |
| PII | 0 | 98.8 | 0.4 | 0.8 | 0 |
| PIII | 61.0 | 4.8 | 0 | 33.0 | 1.2 |
| PIV | 47.2 | 3.3 | 40.4 | 7.5 | 1.6 |
| PV | 10.2 | 44.9 | 35.3 | 8.6 | 1.0 |

Note: In the table, G3, G2 and G1 represent maltotriose, maltose and glucose respectively.

As evident from the results in Table 6, saccharide preparations PI and PII were hardly degraded by alpha-amylase, while saccharide preparations PIII, PIV and PV were degraded by alpha-amylase into smaller oligosaccharides, i.e. saccharides PI and PII, maltotriose, maltose and glucose.

TABLE 7

| Saccharide preparation | Composition in degradation product by alpha-glucosidase (%) | | |
|---|---|---|---|
| | Glucose | Trehalose | Others |
| PI | 36.5 | 63.0 | 0.5 |
| PII | 52.1 | 47.6 | 0.3 |
| PIII | 61.7 | 38.1 | 0.2 |
| PIV | 69.5 | 30.2 | 0.3 |
| PV | 71.4 | 28.3 | 0.3 |

While as evident from the results in Tables 7 and 8, saccharide preparations PI, PII, PIII, PIV and PV were found to be degradable by alpha-glucosidase and acetone-pulverized rat small intestine enzyme into glucose and trehalose as in the case of glucoamylase in Experiment 6.

TABLE 8

| Saccharide preparation | Composition in degradation product by acetone-powdered rat small intestine enzyme (%) | | |
|---|---|---|---|
| | Glucose | Trehalose | Others |
| PI | 37.2 | 62.4 | 0.4 |
| PII | 52.5 | 47.1 | 0.4 |
| PIII | 62.0 | 37.6 | 0.4 |
| PIV | 68.8 | 30.8 | 0.4 |
| PV | 73.4 | 26.5 | 0.1 |

The reaction products by alpha-glucosidase and acetone-pulverized rat small intestine enzyme were further subjected to the pig kidney trehalase commercialized by Sigma Chemical Co., St. Louis, Mo., USA, at pH5.7 and 37° C. for 18 hours and then analyzed for saccharide composition on high-performance liquid chromatography, revealing that in saccharide preparations PI, PII, PIII, PIV and PV, the trehalose which had been formed by alpha-glucosidase or acetone-pulverized rat small intestine enzyme was degradable into glucose by the trehalase.

As described above, (1) The non-reducing saccharide-forming enzyme forms alpha-glycosyl trehaloses from one or more reducing partial starch hydrolysates with glucose polymerization degrees of 3 or higher without changing their glucose polymerization degrees.

(2) Non-reducing saccharide PV yields non-reducing saccharide PII and maltotriose as predominant products when subjected to alpha-amylase, while non-reducing saccharide PII, one trehalose molecule and two glucose molecules when subjected to glucoamylase.

These results suggest that the non-reducing saccharide-forming enzyme according to the present invention provides an entirely novel action mechanism where the reducing ends in reducing partial starch hydrolysates are intramolecularly converted into non-reducing trehalose structures.

Experiment 8

Acute toxicity

Acute toxicity tests were conducted on the non-reducing saccharide preparations PI, PII, PIII, PIV and PV prepared in Experiment 4, where they were orally administered to 7 week-old dd mice. As the result, these non-reducing saccharides were very likely substances of low toxiicity and no animal death was observed when the mice received the possible highest dose. Thus the LD50 of these saccharides was at least 50 g/kg or higher.

Experiment 9

Production of non-reducing saccharide-forming enzyme from Arthrobacter species Q36

Arthrobacter species Q36 (FERM BP-4316) in place of Rhizobium M-11 (FERM BP-4130) was cultivated in fermenter for about 72 hours similarly as in Experiment 1. The activity of non-reducing saccharide-forming enzyme in the culture was about 1.2 units/ml. After assaying similarly as in Experiment 1, the enzymatic activities in the cell suspension and supernatant were about 0.5 units/ml and about 0.7 units/ml respectively.

Experiment 10

Purification of enzyme

The culture, about 18 liters, obtained by the method in Experiment 9 was purified similarly as in Experiment 2. The results in respective purification stages were as shown in Table 9.

After electrophoresing the purified enzyme preparation obtained as eluate of gel filtration in the stages in Table 9 similarly as in Experiment 2 to determine its purity, it was found a single protein band which suggested that the enzyme preparation was electrophoretically homogenous and high in purity.

TABLE 9

| Purification stage | Enzymatic activity (units) | Specific activity (units/mg protein) | Yield (%) |
|---|---|---|---|
| Intact culture | 21,600 | — | 100 |
| Supernatant of disrupted culture | 17,500 | 0.14 | 81 |
| Liquid immediately after salting out by ammonium sulfate | 15,700 | 0.41 | 73 |
| Eluate of ion exchange column chromatography | 12,600 | 6.5 | 58 |
| Eluate of hydrophobic column chromatography | 8,820 | 98 | 41 |
| Eluate of gel filtration | 5,290 | 201 | 24 |

Experiment 11
Properties of enzyme

Figure 5:
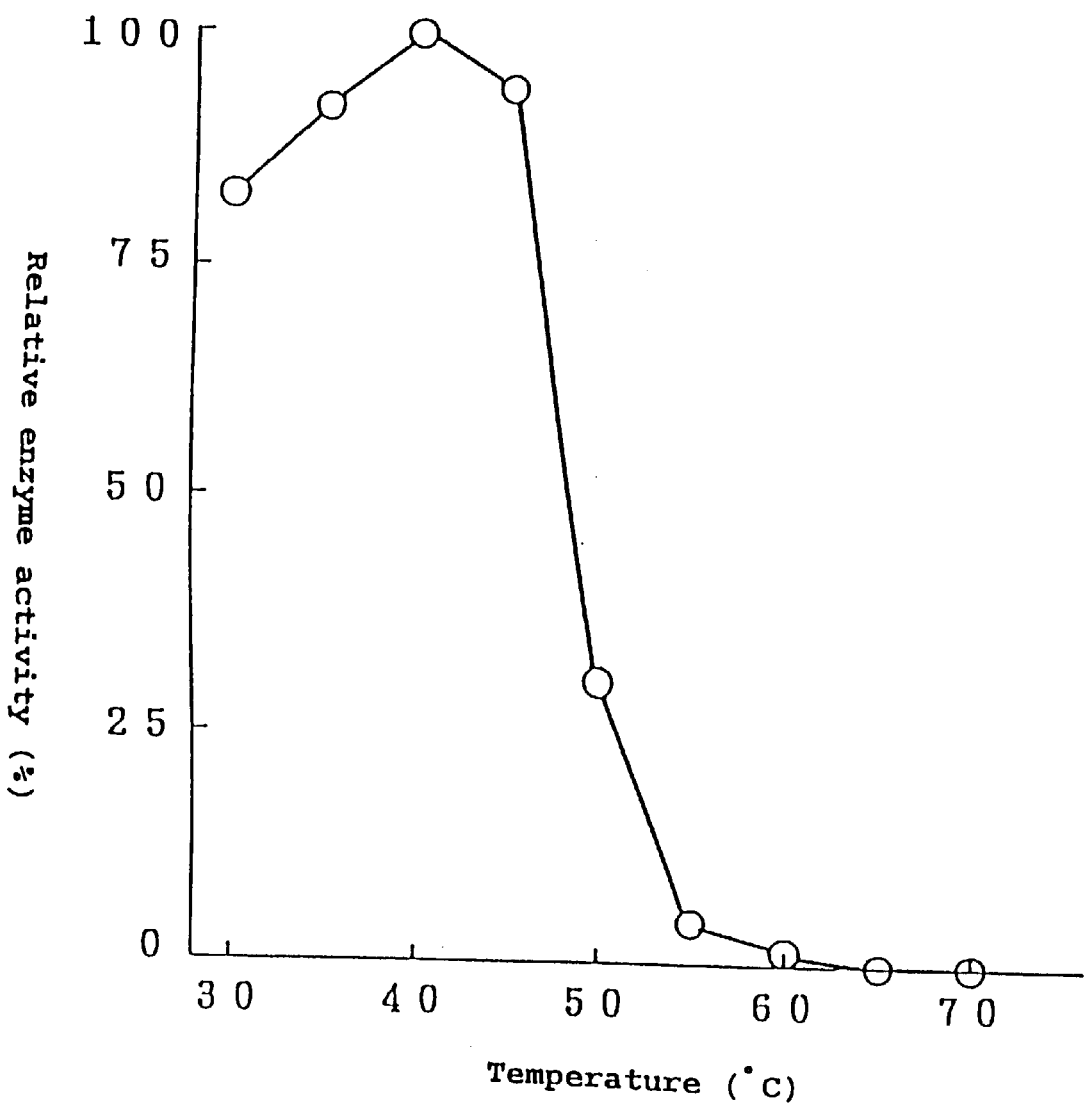
FIG. 5 shows the effect of temperature on the activity of the non-reducing saccharide-forming enzyme derived from Arthrobacter species Q36.
Figure 6:
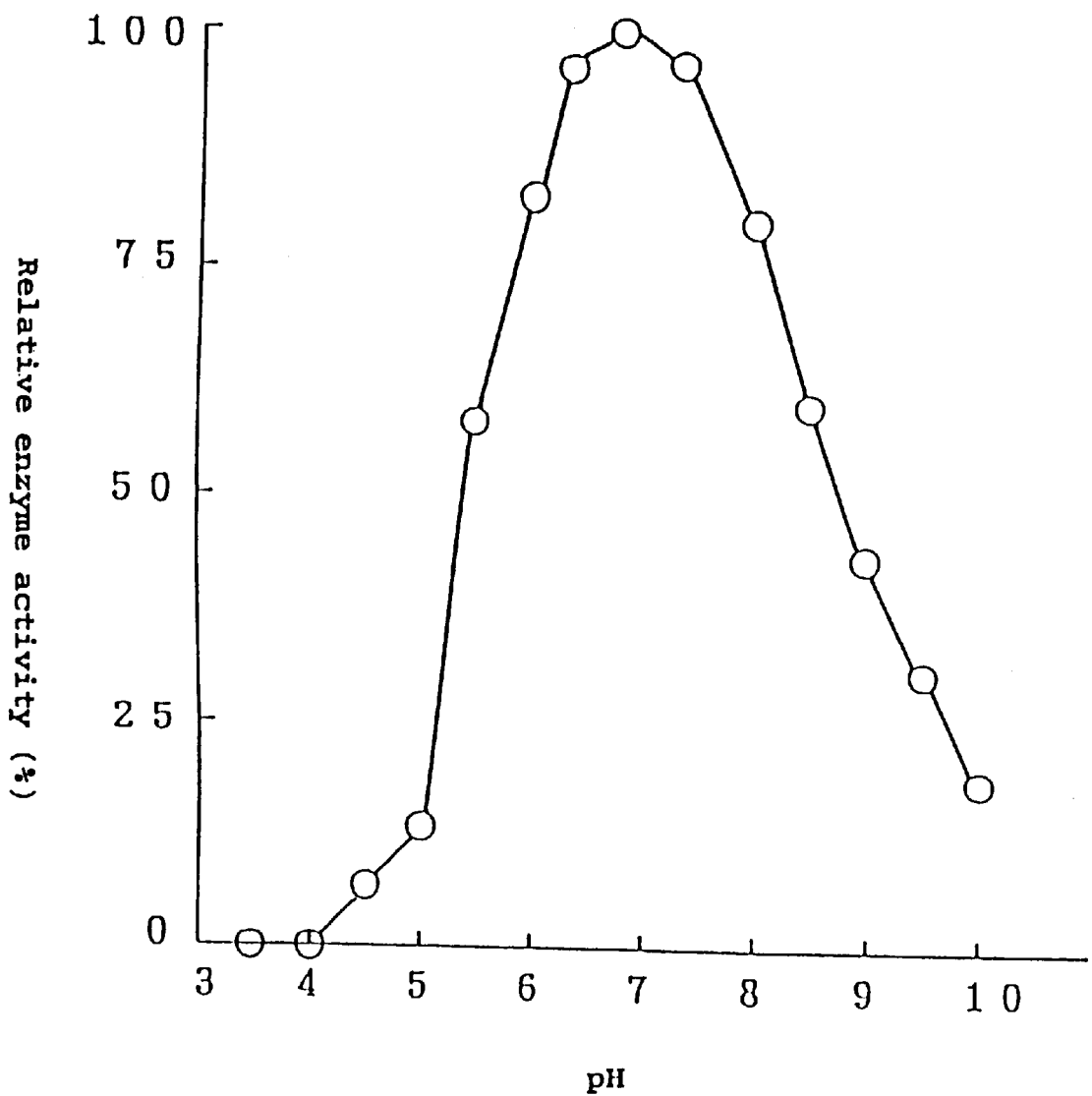
FIG. 6 shows the effect of pH on the activity of the non-reducing saccharide-forming enzyme derived from Arthrobacter species Q36.
Figure 7:
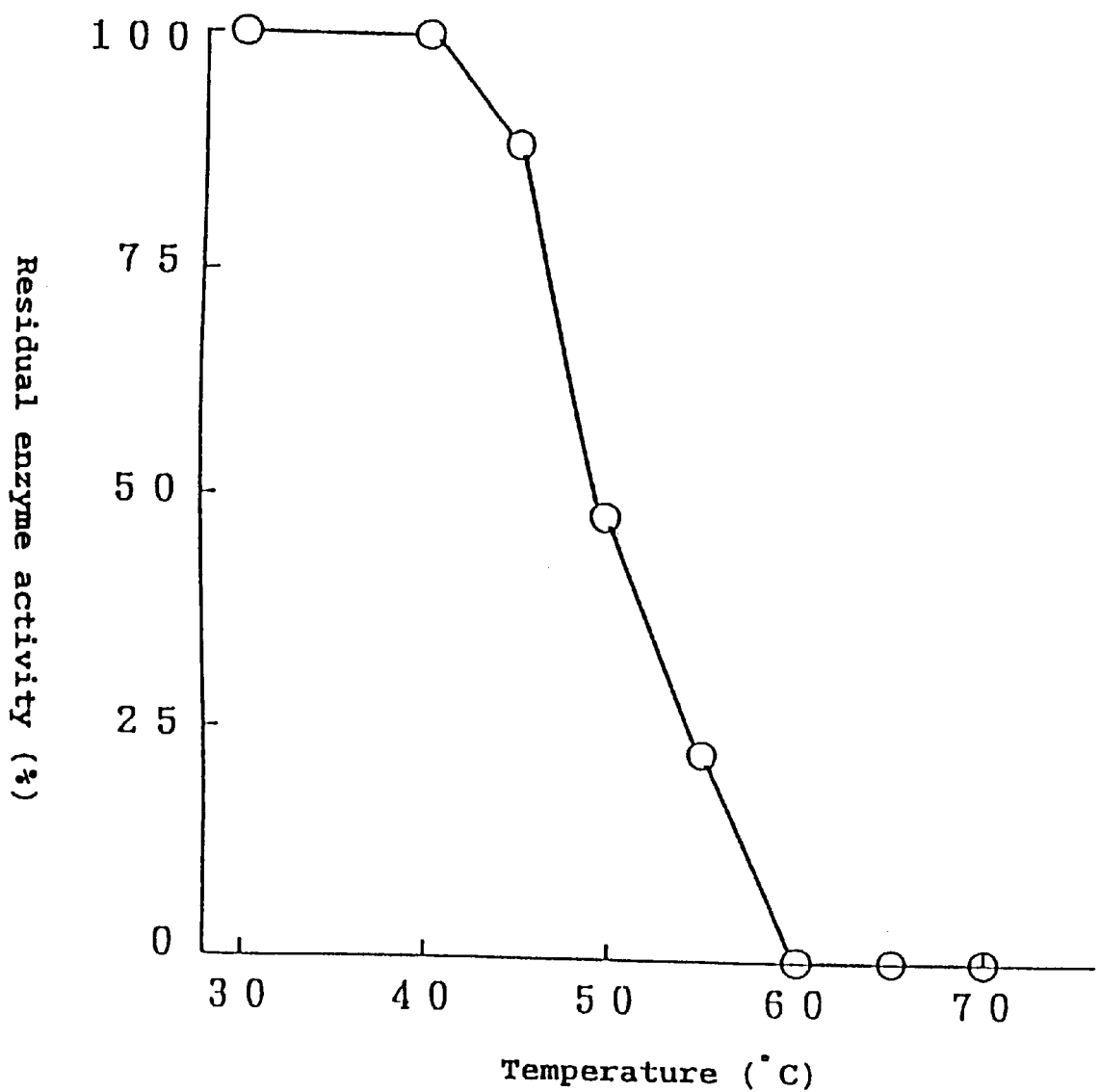
FIG. 7 shows the thermal stability of the non-reducing saccharide-forming enzyme derived from Arthrobacter species Q36.
Figure 8:
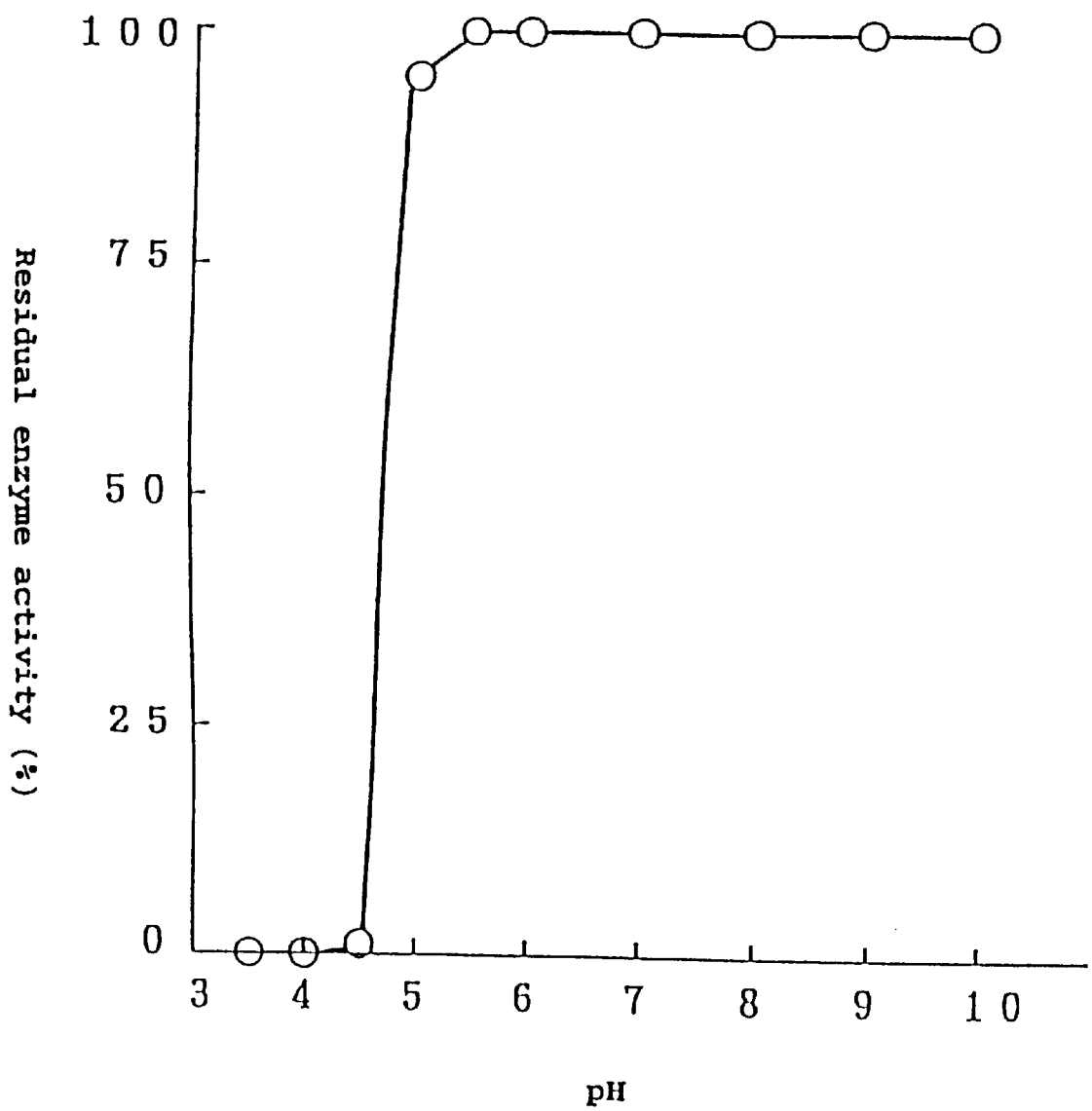
FIG. 8 shows the pH stability of the non-reducing saccharide-forming enzyme derived from Arthrobacter species Q36.

After measuring similarly as in Experiment 3, the purified enzyme preparation obtained in Experiment 10 showed a molecular weight of about 76,000–86,000 daltons. After measuring similarly as in Experiment 3, the purified enzyme preparation showed an isoelectric point at about pI3.6–4.6. Effects of temperature and pH on enzymatic activity and thermal and pH stabilities were tested similarly as in Experiment 3. The results were as shown in FIG. 5 for the effect of temperature, in FIG. 6 for the effect of pH, in FIG. 7 for the thermal stability and in FIG. 8 for the pH stability.

As evident from these Figures, the optimum temperature and pH of the enzyme were around 40° C. and about 6.5–7.0 respectively. The thermal stability was up to about 40° C., while the pH stability, about 6.0–9.5.

Experiment 12
Preparation of non-reducing saccharides

After testing the purified enzyme preparation obtained in Experiment 10 for formation of non-reducing saccharides and confirmation of their structures in accordance with the methods in Experiments 4 and 6, it was found that to form alpha-glycosyl trehaloses from one or more reducing partial starch hydrolysates with glucose polymerization degrees of 3 or higher similarly as the non-reducing saccharide-forming enzyme derived from Rhizobium species M-11.

Experiment 13
Production and properties of non-reducing saccharide-forming enzymes from conventional micro-organisms Among conventional micro-organisms, several micro-organisms in Table 10 which had been confirmed for productivity of non-reducing saccharide-forming enzyme were cultivated at 27° C. for about 72 hours similarly as in Experiment 1 except that *Mycobacterium smegmatis* (ATCC19420) was cultivated at 37° C. The resultant cultures, about 18 liters each, were subjected to cell disruption similarly as in Experiment 2 and the supernatants were salted out with ammonium sulfate, dialyzed and applied to ion exchange column to obtain crude enzyme preparations which were then investigated for properties. The results were as shown in Table 10.

After testing for formation of non-reducing saccharides and confirmation of their structures in accordance with the method in Experiment 12, it was found that each enzyme formed alpha-glycosyl trehaloses from one or more reducing partial starch hydrolysates with glucose polymerization degrees of 3 or higher similarly as the non-reducing saccharide-forming enzyme derived from Rhizobium species M-11.

TABLE 10

| Microorganism | Eluate of ion exchange column | Optimum temperature | Optimum pH | Thermal stability | pH Stability |
|---|---|---|---|---|---|
| Brevibacterium helovolum (ATCC11822) | 2,700 units | about 35° C. | about 6.5 | up to about 35° C. | about 5.5–11 |
| Flavobacterium aquatile (IFO3772) | 216 units | about 35° C. | about 6.5–6.9 | up to about 35° C. | about 6.0–9.5 |
| Micrococcus luteus (IFO3064) | 1,730 units | about 35° C. | about 6.4–6.8 | up to about 35° C. | about 6.5–8.0 |
| Micrococcus roseus (ATCC186) | 1,340 units | about 35° C. | about 6.8–7.2 | up to about 35° C. | about 6.0–11 |
| Curtobacterium citreum (IFO15231) | 1,290 units | about 30° C. | about 6.4–6.8 | up to about 35° C. | about 6.5–7.8 |
| Mycobacterium smegmatis (ATCC19420) | 358 units | about 35° C. | about 6.5 | up to about 35° C. | about 6.0–9.0 |
| Terrabacter tumescens (IFO12960) | 1,050 units | about 35° C. | about 6.5–7.0 | up to about 35° C. | about 6.0–9.5 |
| Rhizobium species M-11 | 11,300 units | about 40° C. | about 7.0 | up to about 40° C. | about 6.0–9.0 |
| Arthrobacter species Q36 | 12,600 units | about 40° C. | about 6.5–7.0 | up to about 40° C. | about 6.0–9.5 |

The following will explain first trehalose-releasing enzymes from novel micro-organisms Rhizobium species M-11 and Arthrobacter species Q36, then those from conventional micro-organisms.

Experiment 14
Production of trehalose-releasing enzyme from Rhizobium species M-11

A liquid culture medium consisting of 2.0 w/v % "PINE-DEX #4", a partial starch hydrolysate commercialized by Matsutani Chemical Industry, Co., Ltd., Kyoto, Japan, 0.5 w/v % pepton, 0.1 w/v % yeast extract, 0.1 w/v % disodium hydrogen phosphate, 0.1 w/v % potassium dihydrogen phosphate and water was adjusted to pH7.0. About 100 ml aliquots of the culture medium were placed in 500 ml flasks, sterilized at 120° C. for 20 minutes in autoclave, cooled, inoculated with a seed culture of Rhizobium species M-11. (FERM BP-4130) and cultivated at 27° C. and 130 rpm for 24 hours to obtain a seed culture.

About 20 liters of a fresh preparation of the same culture medium was placed in 30 liter fermenter, sterilized, cooled to 27° C., inoculated with 1 w/v % seed culture and cultivated for about 72 hours under aeration and agitation conditions while retaining at 27° C. and pH6.0–8.0.

The activity of non-reducing saccharide-forming enzyme in the culture was about 1.5 units/ml, while that of trehalose-releasing enzyme, about 2 units/ml. A portion of the culture was sampled and centrifugally separated into cells and supernatant and the cells were suspended in 50 mM phosphate buffer (pH7.0) to give the same volume as that of the sampled culture, followed by assaying enzymatic activities in the cell suspension and supernatant, revealing that there were found in the cell suspension about 0.6 units/ml non-reducing saccharide-forming enzyme and about 0.8 units/ml trehalose-releasing enzyme, while in the supernatant was found about 0.9 units/ml non-reducing saccharide-forming enzyme and about 1.2 units/ml trehalose-releasing enzyme.

Experiment 15
Purification of enzyme

A culture, about 18 liters, obtained by the method in Experiment 14, was treated in a super high pressure cell disrupter "MINI LABO" for cell disruption. Thirty-minute centrifugation of the resultant at 10,000 rpm gave about 16 liters of supernatant. The supernatant was then added with ammonium sulfate to give a saturation degree of 0.2, allowed to standing at 4° C. for one hour and centrifuged at 10,000 rmp for 30 minutes, followed by recovering the supernatant.

The supernatant was further added with ammonium sulfate to give a saturation degree of 0.6, allowed to stand at 4° C. for 24 hours and centrifuged, followed by recovering the sediment. The sediment was dissolved in 10 mM phosphate buffer (pH7.0), dialyzed against a fresh preparation of the same buffer for 24 hours and centrifuged for removal of insoluble substances. The dialyzed solution, about 360 ml, was divided into two portions which were then separately applied to ion exchange column chromatography on 300 ml "DEAE TOYOPEARL".

Figure 9:
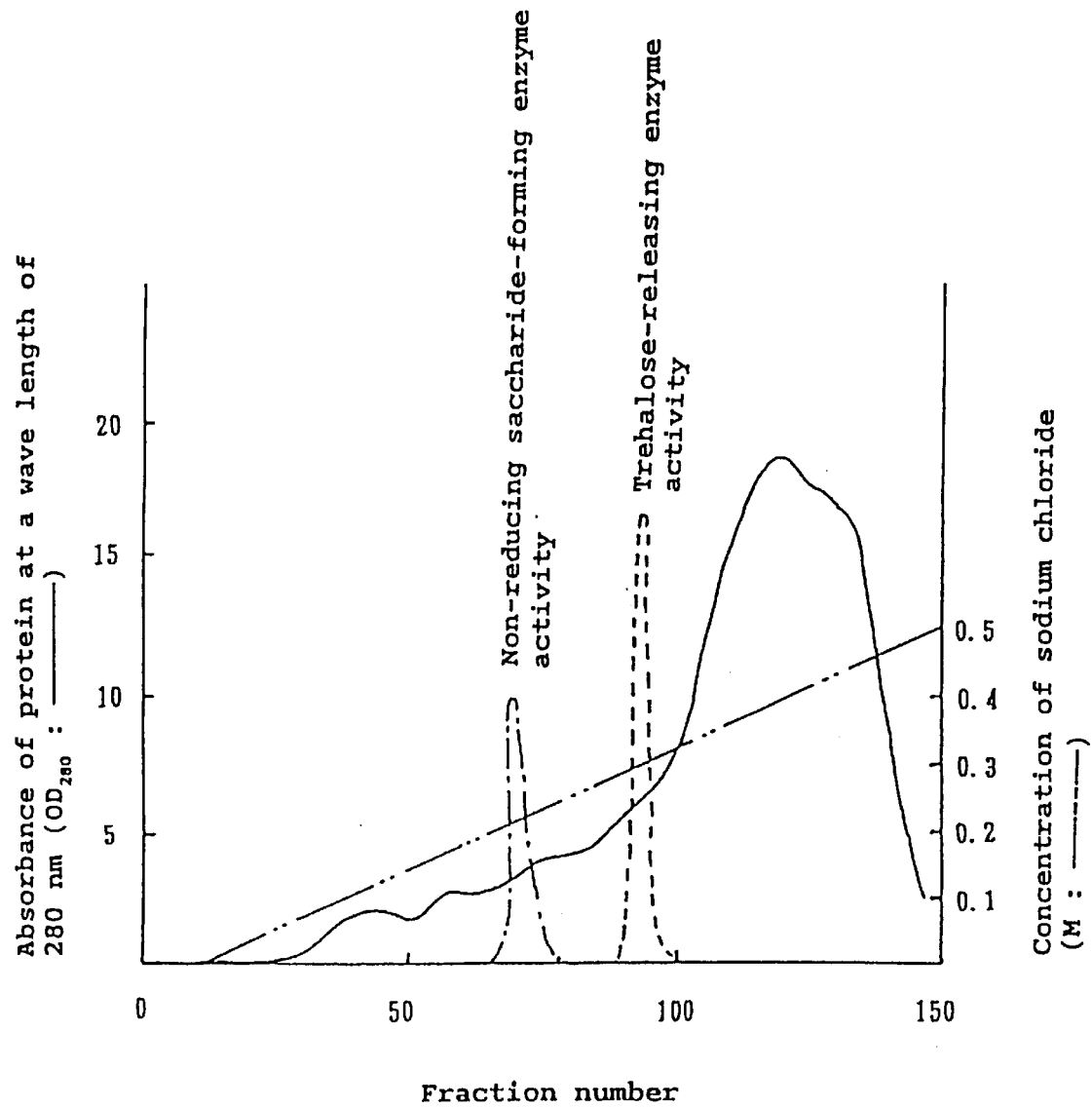
FIG. 9 shows the elution patterns on DEAE TOYOPEARL for the trehalose-releasing enzyme and non-reducing saccharide-forming enzyme both according to the present invention.

Both non-reducing saccharide-forming enzyme and trehalose-releasing enzyme according to the present invention, which had been adsorbed on "DEAE TOYOPEARL", were eluted therefrom at different sodium chloride concentrations when a fresh preparation of the same buffer but additionally containing sodium chloride was passed through the column. The elution pattern from "DEAE TOYOPEARL" was as shown in FIG. 9. The non-reducing saccharide-forming enzyme and trehalose-releasing enzyme were eluted at sodium chloride concentrations of about 0.2M and 0.3M respectively and enzymatically active fractions for respective enzymes were separately recovered and purified.

The fractions with the non-reducing saccharide-forming enzyme was dialyzed against a fresh preparation of the same buffer but additionally containing 2M ammonium sulfate, centrifuged to remove insoluble substances and applied to hydrophobic column chromatography on 300 ml "BUTYL TOYOPEARL 650". The adsorbed enzyme was eluted from the column under a linear gradient decreasing from 2M to 0M for ammonium sulfate, followed by recovering enzymatically active fractions. Subsequent gel filtration chromatography was carried out on 300 ml "TOYOPEARL HW-55" and fractions with non-reducing saccharide-forming enzyme activity were recovered.

Purification of the trehalose-releasing enzyme was carried out as follows: Fractions with trehalose-releasing emzyme activity eluted from "DEAE TOYOPEARL" were dialyzed against a fresh preparation of the same buffer but additionally containing 2M ammonium sulfate and applied to both hydrophobic and gel filtration column chromatography similarly as for the non-reducing saccharide-forming enzyme.

The enzymatic activities, specific activities and yields in respective purification stages were as shown in Table 11 for the non-reducing saccharide-forming enzyme and in Table 12 for the trehalose-releasing enzyme.

After testing both purified non-reducing saccharide-forming enzyme and trehalose-releasing enzyme for purity on electrophoresis using 7.5% polyacrylamide gel, they gave distinct single protein bands, suggesting that both enzyme preparations were electrophoretically homogenous and high in purity.

TABLE 11

| Purification stage | Enzymatic activity (units) | Specific activity (units/mg protein) | Yield (%) |
|---|---|---|---|
| Intact culture | 28,500 | — | 100 |
| Supernatant of disrupted culture | 22,900 | 0.12 | 80 |
| Liquid immediately after salting out by ammonium sulfate | 21,100 | 0.43 | 74 |
| Eluate of ion exchange column chromatography | 15,200 | 6.2 | 53 |
| Eluate of hydrophobic column chromatography | 7,950 | 101 | 28 |
| Eluate of gel filtration | 5,980 | 197 | 21 |

TABLE 12

| Purification stage | Enzymatic activity (units) | Specific activity (units/mg protein) | Yield (%) |
|---|---|---|---|
| Intact culture | 37,400 | — | 100 |
| Supernatant of disrupted culture | 31,500 | 0.17 | 84 |
| Liquid immediately after salting out by ammonium sulfate | 29,200 | 0.60 | 78 |
| Eluate of ion exchange column chromatography | 25,400 | 5.3 | 68 |
| Eluate of hydrophobic column chromatography | 18,700 | 98.5 | 50 |
| Eluate of gel filtration | 11,600 | 240 | 31 |

Experiment 16
Properties of trehalose-releasing enzyme

The purified trehalose-releasing enzyme obtained by the methods in Experiment 15 was electrophoresed on SDS-polyacrylamide gel, gel concentration of 10%, and then compared with the molecular weight markers commercialized by Japan Bio-Rad Laboratories, Tokyo, Japan, which had been electrophoresed on the same gel, revealing that the molecular weight of the enzyme was about 58,000–68,000 daltons.

The purified enzyme preparation was subjected to isoelectric point electrophoresis on polyacrylamide gel and the pH levels in the gel were determined, revealing that the isoelectric point of the enzyme was about 3.3–4.3.

Figure 10:
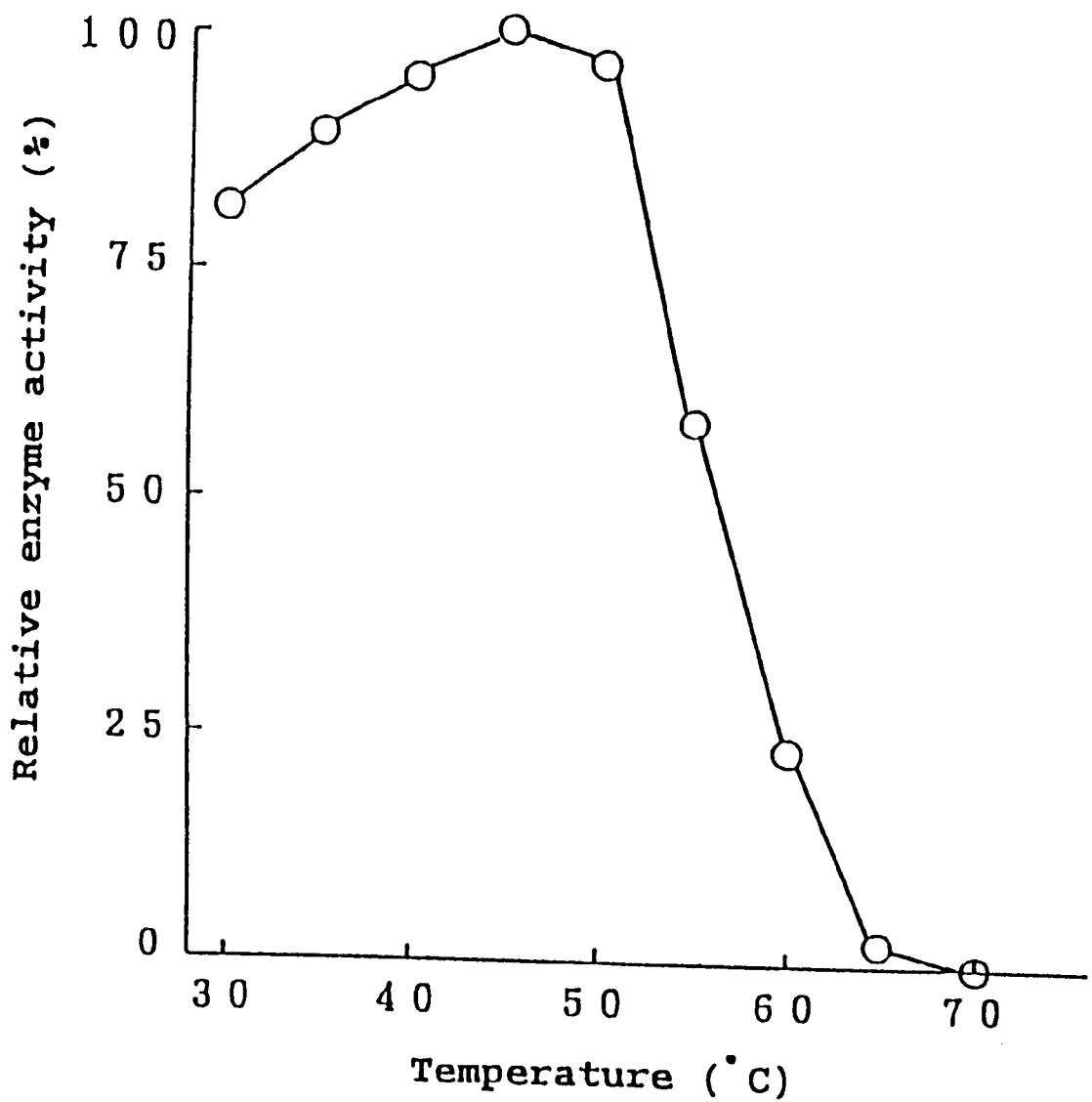
FIG. 10 shows the effect of temperature on the activity of the trehalose-releasing enzyme derived from Rhizobium species M-11.
Figure 11:
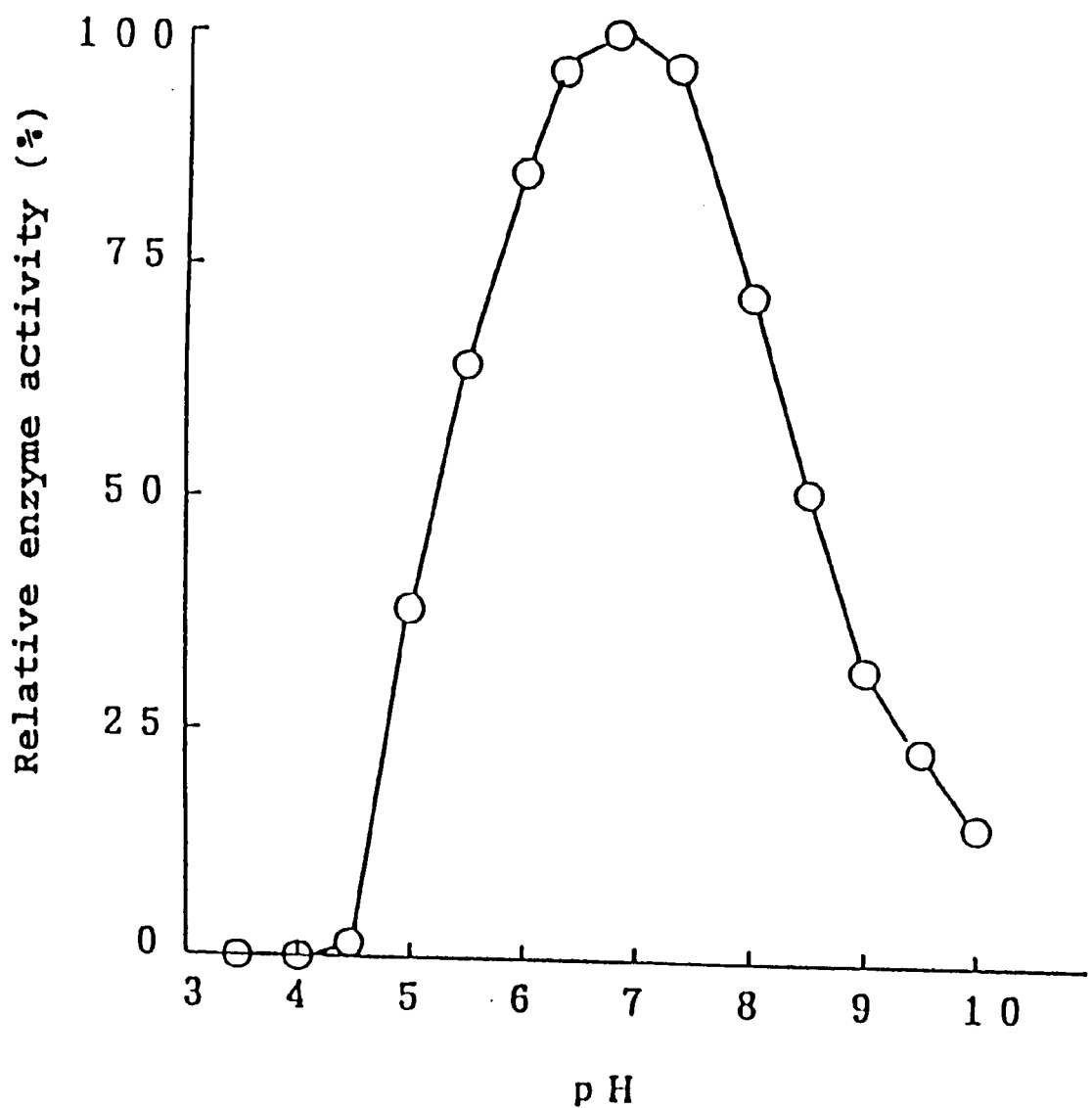
FIG. 11 shows the effect of pH on the activity of the trehalose-releasing enzyme derived from Rhizobium species M-11.
Figure 12:
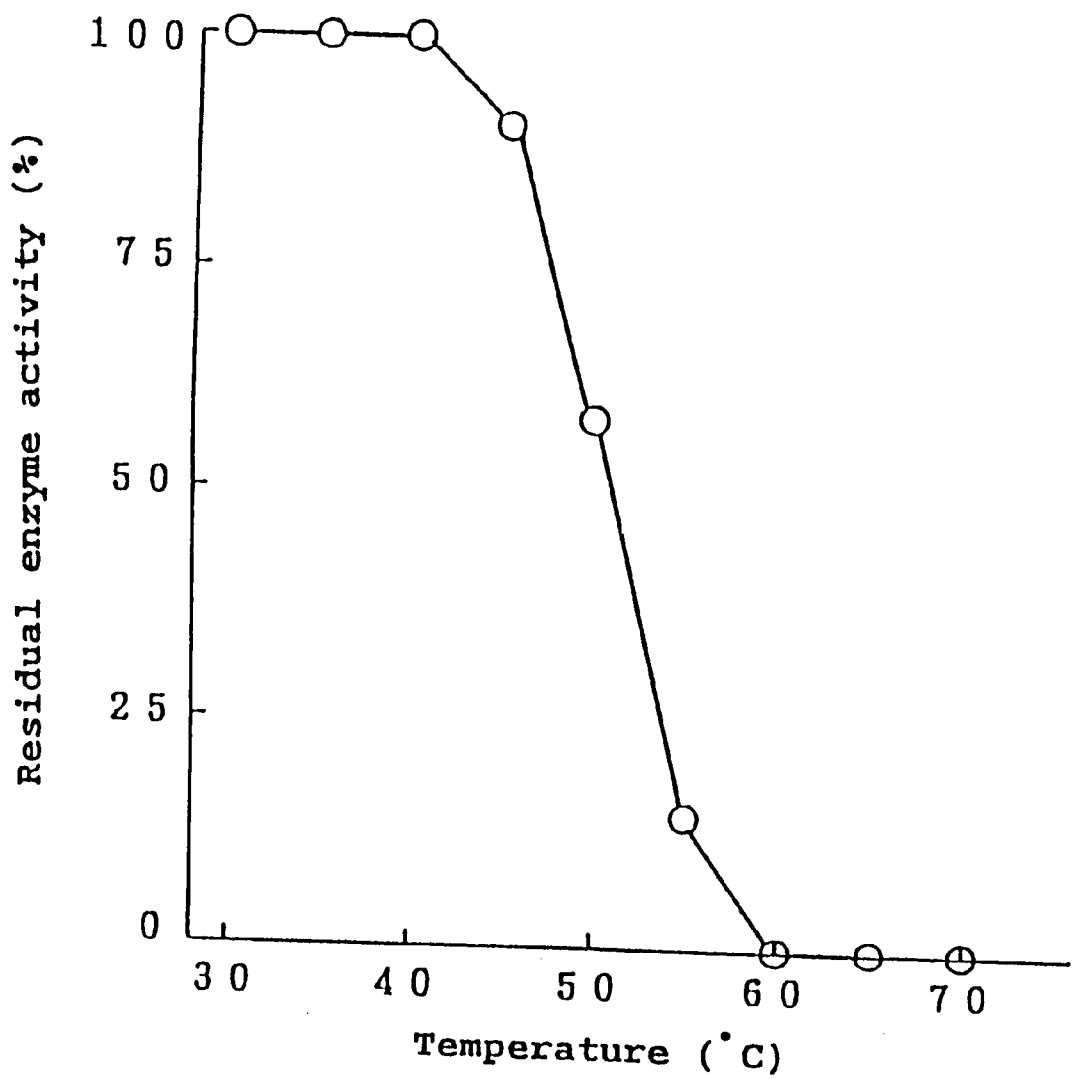
FIG. 12 shows the thermal stability of the trehalose-releasing enzyme derived from Rhizobium species M-11.
Figure 13:
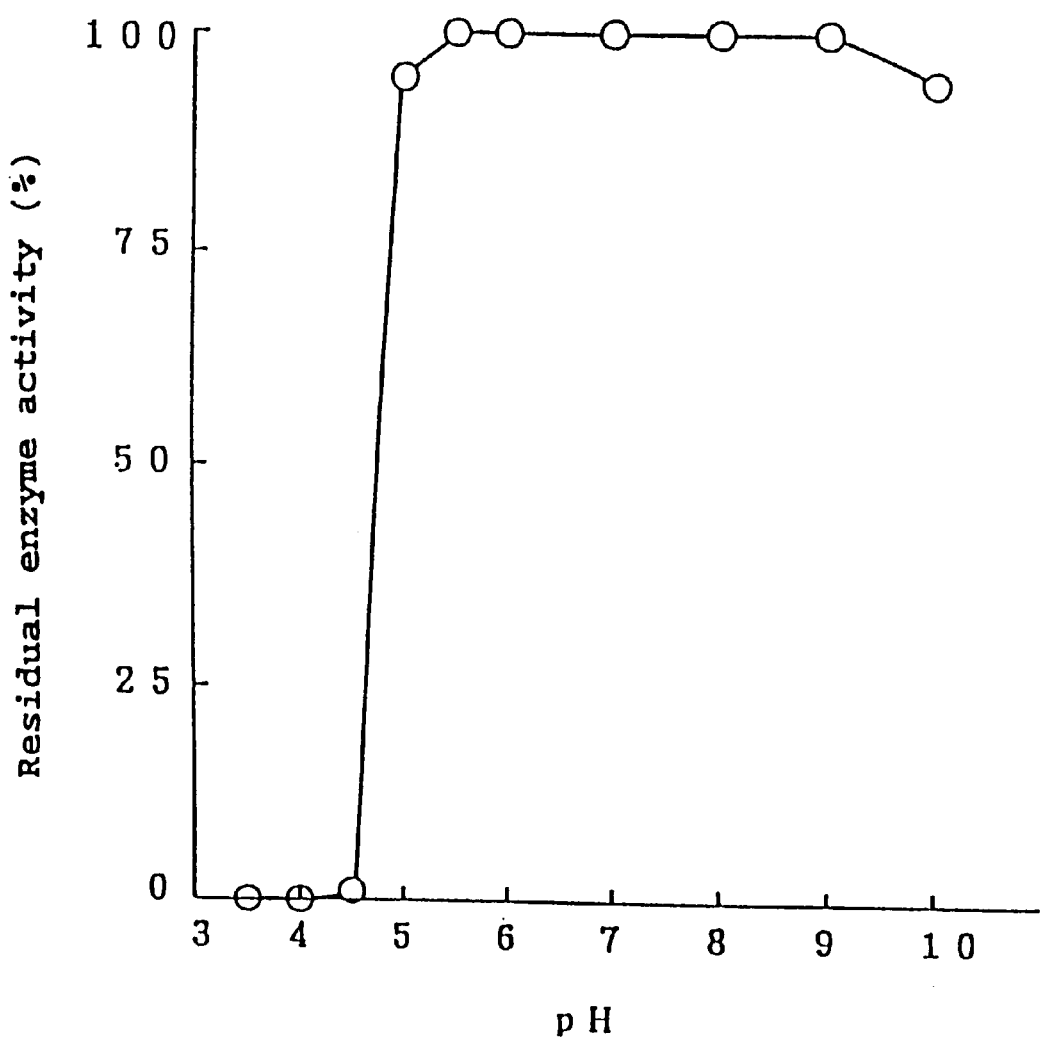
FIG. 13 shows the pH stability of the trehalose-releasing enzyme derived from Rhizobium species M-11.

Effects of temperature and pH on enzymatic activity were tested in accordance with the assay method. The results were as shown in FIG. 10 for the effect of temperature and FIG. 11 for the effect of pH. The optimum temperature was around 45° C. when allowed to react at pH7.0 for 30 minutes, while the optimum pH, about 6.0–7.5 when allowed to react at 40° C. for 30 minutes. The thermal stability was determined by incubating the enzyme in 50 mM phosphate buffer (pH7.0) at different temperatures for 60 minutes, cooling with water and assaying the residual enzymatic activities. While the pH stability was determined by incubating the enzyme in 50 mM phosphate buffer of different pH levels at 25° C. for 16 hours, adjusting to pH7 and assaying the residual enzymatic activities. The results were as shown in FIG. 12 for the thermal stability and in FIG. 13 for the pH stability. The thermal stability of the enzyme was up to about 40° C., while pH stability, about 5–10.

Experiment 17
Preparation of trehalose from alpha-glycosyl trehalose

Alpha-glycosyl trehaloses as substrates were prepared in accordance with the method described in Japanese Patent Application No. 349,216/93. More particularly, 20% aqueous solutions of maltotriose, maltotetraose, maltopentaose, maltohexaose or maltoheptaose as reducing partial starch hydrolysate were added with 2 units/g substrate solid of a purified non-reducing saccharide-forming enzyme obtained by the method in Experiment 15, reacted at 40° C. and pH7.0 for 48 hours, heated for inactivation, filtered, deionized, concentrated in conventional manner and applied to ion exchange column chromatography on a strongly-acidic cation exchange "XT-1016" in sodium form. The ion exchange resin was packed in 3 jacketed-stainless steel columns, inner diameter of 2.0 cm, length of 1 m, and the columns were cascaded, loaded with 5 v/v % reaction saccharide liquid against the resin and injected with 55° C. water at SV0.13 for fractionation while keeping the temperature inside the columns at 55° C., thus obtaining high-purity preparations of non-reducing saccharides with glucose polymerization degrees of 3 or higher. Among these high-purity preparations, the glucosyl trehalose preparation had a purity of 97.6%; the maltosyl trehalose preparation, 98.6%, the maltotriosyl trehalose preparation, 99.6%; the maltotetraosyl trehalose preparation, 98.3%; and the maltopentaosyl trehalose, 98.1%.

TABLE 13

| Substrate | Reaction product | Elution time on HPLC (min) | Composition (%) |
|---|---|---|---|
| Glucosyl trehalose | Trehalose | 27.4 | 17.5 |
| | Glucose | 33.8 | 6.5 |
| | Glucosyl trehalose | 23.3 | 76.0 |
| Maltosyl trehalose | Trehalose | 27.4 | 44.3 |
| | Maltose | 28.7 | 44.4 |
| | Maltosyl trehalose | 21.6 | 11.3 |

TABLE 13-continued

| Substrate | Reaction product | Elution time on HPLC (min) | Composition (%) |
|---|---|---|---|
| Maltotriosyl trehalose | Trehalose | 27.4 | 39.5 |
| | Maltotriose | 25.9 | 60.0 |
| | Maltotriosyl trehalose | 19.7 | 0.5 |
| Maltotetraosyl trehalose | Trehalose | 27.4 | 34.2 |
| | Maltotetraose | 24.1 | 65.5 |
| | Maltotetraosyl trehalose | 18.7 | 0.3 |
| Maltopentaosyl trehalose | Trehalose | 27.4 | 29.1 |
| | Maltopentaose | 22.6 | 70.6 |
| | Maltopentaosyl trehalose | 17.8 | 0.3 |
| Maltotriose | Maltotriose | 25.9 | 100 |
| Maltotetraose | Maltotetraose | 24.1 | 100 |
| Maltopentaose | Maltopentaose | 22.6 | 100 |
| Maltohexaose | Maltohexaose | 21.8 | 100 |
| Maltoheptaose | Maltoheptaose | 21.0 | 100 |

20% Aqueous solutions of these five types of non-reducing saccharides or alpha-glycosyl trehaloses were prepared, added with 2 units/g substrate solid of the purified trehalose-releasing enzyme obtained in Experiment 15, reacted at 40° C. and pH7.0 for 48 hours, deionized and subjected to high-performance liquid chromatography on "WAKO BEADS WB-T-330" for analysis of reaction products. As control, maltotriose, maltotetraose, maltopentaose, maltohexaose and maltoheptaose were subjected to the purified trehalose-releasing enzyme similarly as above and then analyzed on high-performance liquid chromatography. The results were as shown in Table 13.

As evident from the results in Table 13,
(1) The trehalose-releasing enzyme specifically hydrolyzes the linkages between trehalose moieties and glycosyl moieties in alpha-glycosyl trehaloses to form trehalose and reducing saccharides with glucose polymerization degrees of 1 or higher.
(2) Maltooligosaccharides are not susceptible at all to the trehalose-releasing enzyme.

With these results, it would be concluded that the trehalose-releasing enzyme according to the present invention provides an entirely novel action mechanism where the linkages between the trehalose moieties and glycosyl moieties in alpha-glycosyl trehaloses are very specifically hydrolyzed to release trehalose.

In order to purify trehalose from respective reaction products, they were decolored, deionized, concentrated and subjected to column fractionation on a strongly-acidic cation exchange of sodium form "XT-1016", followed by recovering high-purity fractions with trehalose contents of 97% or higher. The fractions were then concentrated to about 65% and allowed to standing at 25° C. for 2 days to crystallize out crystalline trehalose hydrate which was then separated and dried in vacuo to obtain a high-purity preparation with a trehalose content of 99% or higher. The yields against respective starting substrates on dry solid basis were as follows: from glycosyl trehalose, 9.5%; from maltosyl trehalose, 14.9%; from maltotriosyl trehalose, 16.0%; from maltotetraosyl trehalose, 18.5%; and from maltopentaosyl trehalose, 17.7%. The obtained trehalose was compared for melting point, melting heat, specific rotation, infrared absorption spectrum, powder x-ray diffraction pattern and degradation by the trehalase derived from the pig kidney commercialized by Sigma Chemical Co., St. Louis, Mo., USA, with the trehalose reagent as standard available from Wako Pure Chemical Industries, Ltd., Osaka, Japan, revealing that the high-purity trehalose preparations as tested exhibited a melting point of 97.0±0.5° C., a melting heat of 57.8±1.2 KJ/mol and a specific rotation of +182±1° which were all in good agreement with those observed in the trehalose reagent, as well as that their infrared spectra and powder x-ray diffraction patterns were also in good agreement with those of the trehalose reagent. Further the high-purity trehalose preparations were degraded by the trehalase derived from pig kidney similarly as the trehalose reagent. As evident from the above results, the saccharides formed by subjecting alpha-glycosyl trehaloses to the trehalose-releasing enzyme were identified to be trehalose.

Experiment 18

Preparation of trehalose from reducing partial starch hydrolysates

Waxy cornstarch in 5% suspension was gelatinized by heating, adjusted to pH4.5 and 50° C., added with 4,000 units/g starch solid of the isoamylase commercialized by Hayashibara Biochemical Laboratories, Inc., Okayama, Japan, and reacted for 20 hours. The reaction mixture was autoclaved at 120° C. for 10 minutes, cooled to 60° C. and subjected to gel filtration chromatography on 750 ml "TOYOPEARL HW-50S", a product of Tosoh Corp., Tokyo, Japan, to obtain reducing partial starch hydrolysates with glucose polymerization degrees of 10–35.

The reducing partial starch hydrolysates thus obtained and maltotriose as reducing partial starch hydrolysate with a glucose polymerization degree of 3 were diluted to 1% in 10 mM phosphate buffer (pH7.0), added with the purified non-reducing saccharide-forming enzyme and trehalose-releasing enzyme both prepared by the methods in Experiment 15 in respective amounts of 4 units/g substrate solid, reacted at 40° C. for 24 hours, sampled in small portions, deionized and analyzed on high-performance liquid chromatography for reaction products.

The remaining reaction mixtures were adjusted to 50° C. and pH4.5, added with 50 units/g substrate solid of the glucoamylase commercialized by Seikagaku Corp., Tokyo, Japan, reacted for 24 hours, deionized similarly as above and analyzed on high-performance liquid chromatography for reaction products. The results were as shown in Table 14.

As shown in Table 14, the yields for trehalose from maltotriose by the non-reducing saccharide-forming enzyme and trehalose-releasing enzyme were low, i.e. 4.2%, while the reducing partial starch hydrolysates with glucose polymerization degrees of 10–34.1 marked high yields, i.e. 66.1–80.8%. Further it was revealed that higher the glucose polymerization degree of reducing partial starch hydrolysate as material, a higher trehalose purity was attainable. Also was revealed that the purity of trehalose was further increased by subjecting to glucoamylase the reaction mixture which has been exposed to both enzymes to degrade the residual alpha-glycosyl trehalose with glucose polymerization degrees of 3 or higher into trehalose and glucose.

TABLE 14

| Glucose polymerization degree of reducing partial starch hydrolysate | Reaction product | Composition (%) | |
|---|---|---|---|
| | | After reaction by NRSF and TR enzymes | After reaction by glucoamylase |
| 34.1 | Trehalose | 80.8 | 83.5 |
| | Glucose | 0.2 | 16.5 |
| | Reducing oligosaccharides | 14.4 | 0.0 |
| | Glycosyl trehaloses | 4.6 | 0.1 |
| 26.2 | Trehalose | 79.7 | 82.5 |
| | Glucose | 0.2 | 17.5 |
| | Reducing oligosaccharides | 15.3 | 0.0 |
| | Glycosyl trehaloses | 4.8 | 0.0 |
| 18.1 | Trehalose | 77.7 | 80.7 |
| | Glucose | 0.2 | 19.3 |
| | Reducing oligosaccharides | 17.0 | 0.0 |
| | Glycosyl trehaloses | 5.1 | 0.0 |
| 15.2 | Trehalose | 75.0 | 78.5 |
| | Glucose | 0.3 | 21.5 |
| | Reducing oligosaccharides | 18.6 | 0.0 |
| | Glycosyl trehaloses | 6.1 | 0.0 |
| 10.0 | Trehalose | 66.1 | 70.1 |
| | Glucose | 0.3 | 29.9 |
| | Reducing oligosaccharides | 27.6 | 0.0 |
| | Glycosyl trehaloses | 7.7 | 0.0 |
| 3 (Maltotriose) | Trehalose | 4.2 | 20.8 |
| | Glucose | 2.1 | 79.2 |
| | Maltotriose | 65.0 | 0.0 |
| | Glucosyl trehalose | 28.7 | 0.0 |

Note: In the Table, NRSF and TR enzymes mean non-reducing saccharide-forming and trehalose-releasing enzymes respectively. Glycosyl trehalose means non-reducing saccharides with glucose polymerization degrees of 3 or higher.

Experiment 19

Maillard reaction

10% High-purity trehalose preparation, purity of 99.5%, obtained by the method in Experiment 17 and 1% glycine in 50 mM phosphate buffer (pH7.0) was incubated at 100° C. for 90 minutes, cooled and measured in 1cm cuvette for absorbance at 480 nm. As control, glucose and maltose were treated similarly as above and then measured for absorbance at 480 nm. The results were as shown in Table 15.

TABLE 15

| Saccharide preparation | Coloration degree as tested at 480 nm | Remarks |
|---|---|---|
| Trehalose | 0.006 | Present invention |
| Glucose | 1.671 | Control |
| Maltose | 0.926 | Control |

As evident from the results in Table 15, the trehalose preparation caused a trace coloration by Maillard reaction which was up to only 0.4–0.6% of those found in glucose and maltose, revealing that the trehalose preparation according to the present invention was a saccharide which would cause less Maillard reaction. Thus the saccharide less damage amino acids when mixed therewith.

Experiment 20
Test for assimilation in vivo

In accordance with the method reported by Atsuji et al., Rinsho Eiyo (Clinical Nutrition), Vol.41, No. 2, pp.200–208 (1972), 30 g of a high-purity trehalose preparation, purity of 99.5%, obtained by the method in Experiment 17 was prepared into 20 w/v % aqueous solution and orally administered to healthy men, age of 26, 27, 28, 29, 30 or 31 years, after which their bloods were periodically sampled and measured for blood sugar and insulin levels. Glucose was used as control. As the result, trehalose behaved similarly as glucose did, and the blood sugar and insulin levels reached maxima about 0.5–1 hour after administration. Thus it was confirmed that trehalose was readily digested and absorbed and then metabolized and utilized as energy source.

Experiment 21
Acute toxicity test

An acute toxicity test was conducted on a high-purity trehalose preparation obtained by the method in Experiment 17, purity of 99.5%, where it was orally administered in mice. As the result, trehalose caused no death even in the possible highest dose. Thus its LD50 would be briefly 50 g/kg or higher.

Experiment 22
Production of trehalose-releasing enzyme from Arthrobacter species Q36

Arthrobacter species Q36 (FERM BP-4316) in place of Rhizobium species M-11 (FERM BP-4130) was cultivated in fermenter for about 72 hours similarly as in Experiment 14. The activity of non-reducing saccharide-forming enzyme in the culture was about 1.3 units/ml, while that of the trehalose-releasing enzyme according to the present invention was about 1.8 units/ml. After assaying the enzymatic activities in the cell suspension and supernatant similarly as in Experiment 14, there were found in the cell suspension about 0.5 units/ml non-reducing saccharide-forming enzyme and about 0.5 units/ml trehalose-releasing enzyme, while in the supernatant were found about 0.8 units/ml non-reducing saccharide-forming enzyme and about 1.3 units/ml trehalose-releasing enzyme.

Experiment 23
Purification of enzyme

A culture, about 18 liters, obtained by the method in Experiment 22 was purified similarly as in Experiment 15. The results in respective purification stages were as shown in Table 16 for the non-reducing saccharide-forming enzyme and in Table 17 for the trehalose-releasing enzyme.

TABLE 16

| Purification stage | Enzymatic activity (units) | Specific activity (units/mg protein) | Yield (%) |
|---|---|---|---|
| Intact culture | 23,700 | — | 100 |
| Supernatant of disrupted culture | 22,400 | 0.15 | 95 |
| Liquid immediately after salting out by ammonium sulfate | 20,200 | 0.51 | 85 |
| Eluate of ion exchange column chromatography | 15,100 | 6.5 | 64 |
| Eluate of hydrophobic column chromatography | 8,450 | 115 | 36 |
| Eluate of gel filtration | 6,120 | 217 | 26 |

The purified non-reducing saccharide-forming enzyme and trehalose-releasing enzyme obtained as eluates of gel filtration in the stages in Tables 16 and 17 were electrophoresed similarly as in Experiment 15 for determination of purity, revealing that the protein bands were single and both purified enzymes were electrophoretically homogenous and high in purity.

TABLE 17

| Purification stage | Enzymatic activity (units) | Specific activity (units/mg protein) | Yield (%) |
|---|---|---|---|
| Intact culture | 32,500 | — | 100 |
| Supernatant of disrupted culture | 30,100 | 0.19 | 93 |
| Liquid immediately after salting out by ammonium sulfate | 25,400 | 0.72 | 78 |
| Eluate of ion exchange column chromatography | 22,700 | 22.3 | 70 |
| Eluate of hydrophobic column chromatography | 15,200 | 215 | 47 |
| Eluate of gel filtration | 11,600 | 497 | 36 |

Experiment 24
Properties of enzyme

Figure 14:
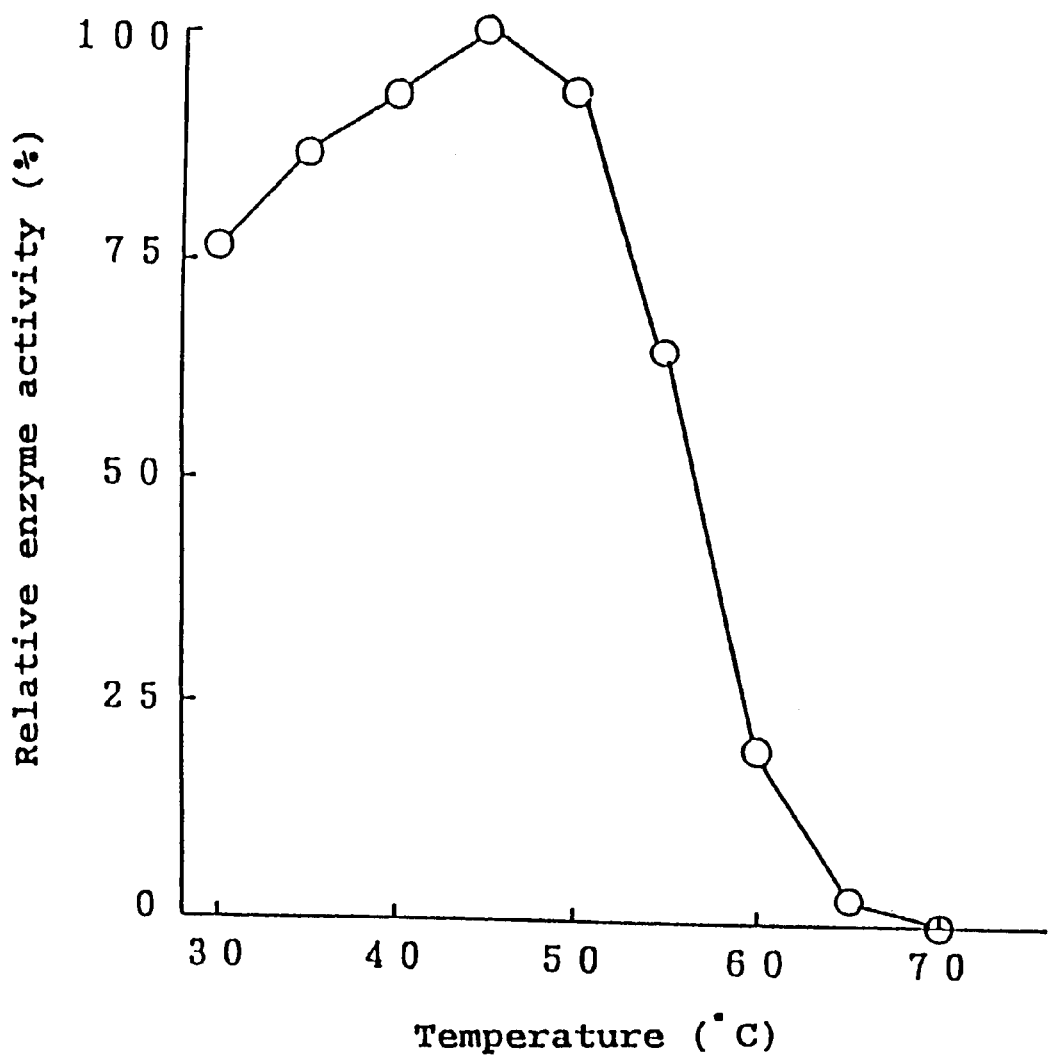
FIG. 14 shows the effect of temperature on the activity of the trehalose-releasing enzyme derived from Arthrobacter species Q36.
Figure 15:
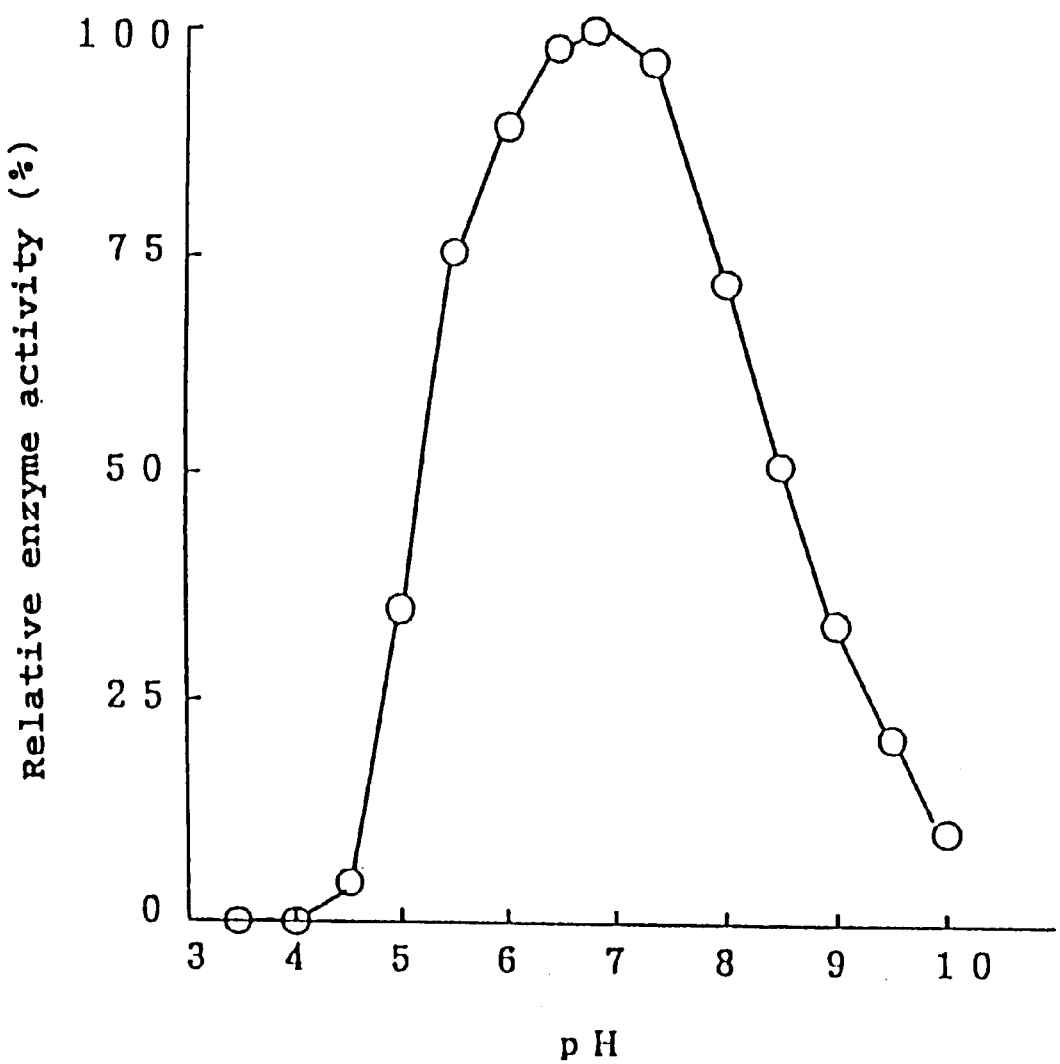
FIG. 15 shows the effect of pH on the activity of the trehalose-releasing enzyme derived from Arthrobacter species Q36.
Figure 16:
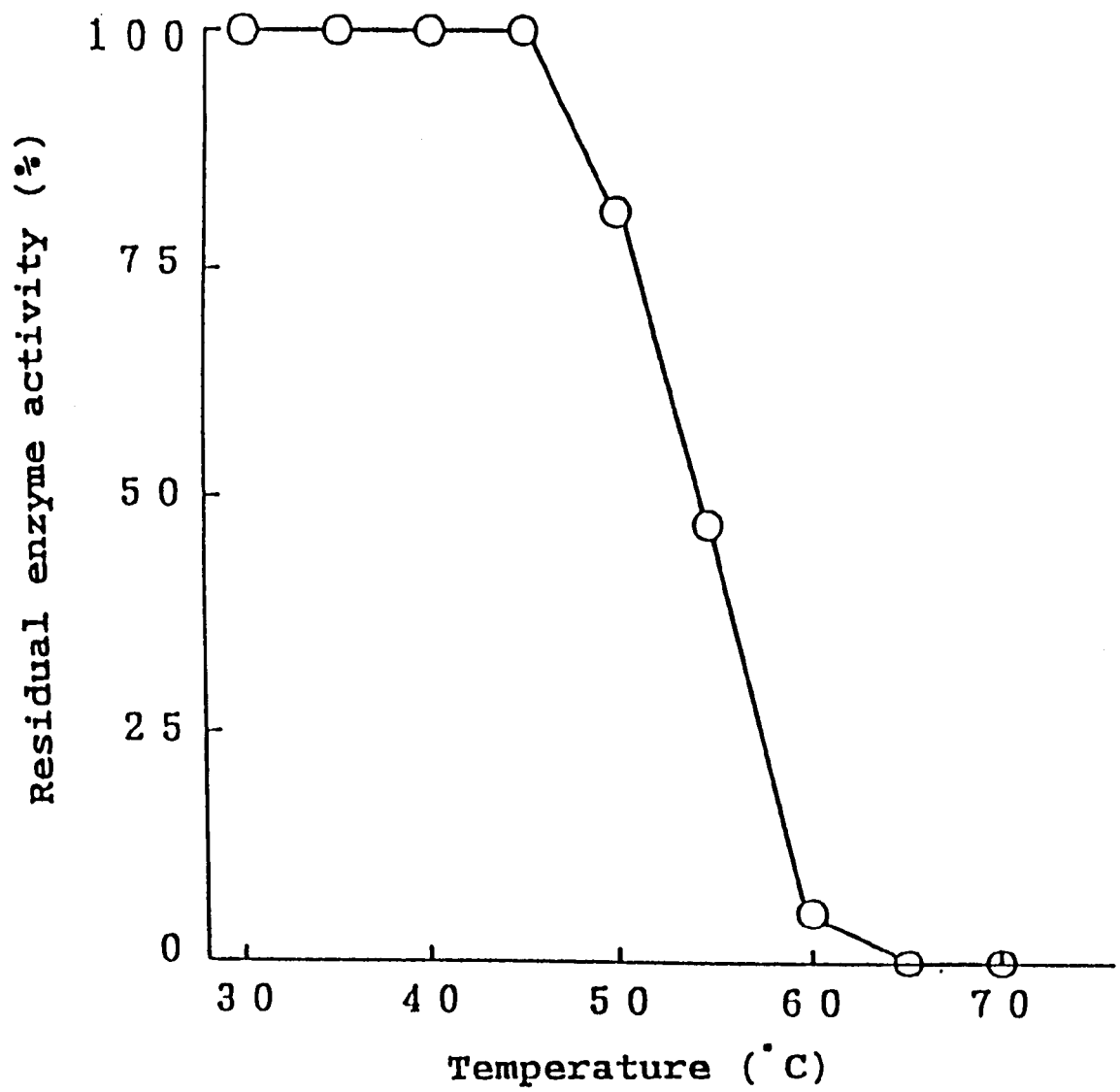
FIG. 16 shows the thermal stability of the trehalose-releasing enzyme derived from Arthrobacter species Q36.
Figure 17:
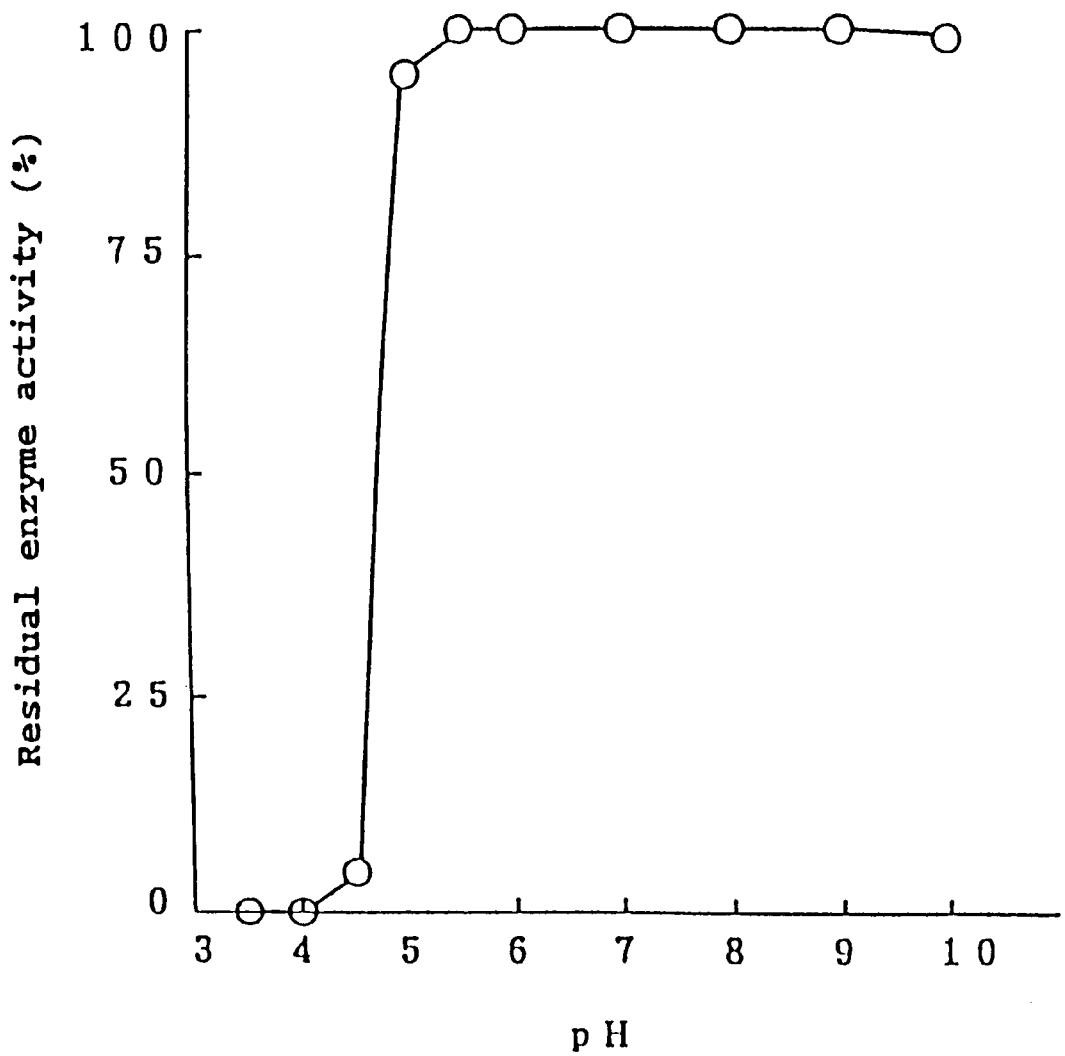
FIG. 17 shows the pH stability of the trehalose-releasing enzyme derived from Arthrobacter species Q36.

After measuring on SDS-polyacrylamide gel electrophoresis similarly as in Experiment 16, the molecular weight of a purified trehalose-releasing enzyme obtained by the method in Experiment 23 was about 57,000–67,000 daltons. After testing the enzyme similarly as in Experiment 3, its isoelectric point was about 3.6–4.6. Effects of temperature and pH and thermal and pH stabilities of the enzyme were determined similarly as in Experiment 16. The results were as shown in FIG. 14 for the effect of temperature, in FIG. 15 for the effect of pH, in FIG. 16 for the thermal stability and in FIG. 17 for the pH stability.

As evident from the Figures, the optimum temperature of the enzyme was around 45° C., while the optimum pH, about 6.0–7.5. The thermal stability was up to about 45° C., while the pH stability, about 5.0–10.0.

Experiment 25
Preparation of trehalose from alpha-glycosyl trehalose

A purified enzyme obtained by the method in Experiment 23 was tested for formation of trehalose from alpha-glycosyl trehaloses with glucose polymerization degrees of 3 or higher in accordance with the method in Experiment 17, revealing that the enzyme released trehalose from alpha-glycosyl trehaloses similarly as the trehalose-releasing enzyme derived from Rhizobium species M-11.

Experiment 26
Production and Properties of trehalose-releasing enzyme from conventional micro-organisms Among conventional micro-organisms, Brevibacterium helobolum (ATCC11822) and Micrococcus roseus (ATCC186) which had been confirmed for production of the trehalose-releasing enzyme according to the present invention were cultivated at 27° C. in fermenter for 72 hours similarly as in Experiment 14. Respective cultures, about 18 liters each, were treated in cell disrupter and the supernatant was centrifugally recovered and subjected to salting out by ammonium sulfate, dialysis and ion exchange column chromatography in the given order, followed by characterizing the obtained partially purified enzyme preparations. The results are given in Table 18 along with those for Rhizobium species M-11 and Arthrobacter species Q36.

These partially purified enzymes derived from conventional micro-organisms were further tested in accordance with the method in Experiment 25 for formation of trehalose from alpha-glycosyl trehaloses with glucose polymerization degrees of 3 or higher, revealing that they released trehalose from alpha-glycosyl trehaloses similarly as the trehalose-releasing enzyme derived from Rhizobium species M-11.

starch liquefied solutions were subjected only to the non-reducing saccharide-forming enzyme and trehalose-releasing enzyme similarly as above and then analyzed on high-performance liquid chromatography. The results were as shown in Table 19.

TABLE 19

| Ratio (%) of alpha-amylase against starch | DE | Combination of enzymes | | | |
|---|---|---|---|---|---|
| | | N + T | N + T + D | N + T + C | N + T + C + D |
| 0.1 | 2.5 | 21.3 | 79.6 | 76.2 | 84.3 |
| 0.4 | 4.8 | 22.5 | 69.7 | 67.7 | 76.9 |
| 0.6 | 7.8 | 23.3 | 63.2 | 59.1 | 68.2 |
| 1.0 | 12.5 | 23.7 | 56.0 | 51.3 | 62.5 |
| 1.2 | 14.8 | 25.3 | 50.3 | 44.7 | 58.4 |
| 1.5 | 17.3 | 22.4 | 44.2 | 39.2 | 48.3 |
| 2.0 | 20.5 | 18.6 | 38.4 | 34.9 | 46.1 |

Note: In the Table, N, T, D and C represent non-reducing saccharide-forming enzyme, trehalose-releasing enzyme, starch-debranching enzyme and cyclomaltodextrin glucanotransferase respectively.

As evident from the results in Table 19, it was found that to produce high-trehalose content saccharides from starches,

TABLE 18

| Microorganism | Eluate of ion exchange column | Optimum Temperature | Optimum pH | Thermal stability | pH Stability |
|---|---|---|---|---|---|
| Brevibacterium helobolum (ATCC11822) | 6,070 units | about 40° C. | about 6.5–6.8 | up to about 40° C. | about 5.5–9.5 |
| Micrococcus roseus (ATCC186) | 3,010 units | about 35° C. | about 6.8 | up to about 30° C. | about 6.5–7.2 |
| Rhizobium species M-11 | 25,400 units | about 45° C. | about 6.0–7.5 | up to about 40° C. | about 5.0–10.0 |
| Arthrobacter species Q36 | 22,700 units | about 45° C. | about 6.0–7.5 | up to about 45° C. | about 5.0–10.0 |

Experiment 27
Effects of starch liquefaction degree and types of enzymes on the production of high-trehalose content saccharides To produce high-trehalose content saccharides from starch, effects of starch liquefaction degree and combinations of enzymes were studied. Cornstarch in 20% suspension was adjusted to pH6.5 by the addition of 0.1% calcium carbonate, added with 0.1–2.0% against starch solid of "TERMAMYL", an alpha-amylase commercialized by Novo Industri AS, Copenhagen, Denmark, reacted at 95° C. for 15 minutes and kept at 120° C. for 10 minutes in autoclave to obtain liquefied starch solutions with DE2.5–20.5 which were then immediately cooled, added with 5 units/g starch solid of a purified non-reducing saccharide-forming enzyme prepared by the method in Experiment 2, 10 units/g starch solid of a purified trehalose-releasing enzyme prepared by the method in Experiment 15 along with 500 units/g starch solid of isoamylase, a type of starch-debranching enzyme, and 5 units/g starch solid of cyclomaltodextrin glucanotransferase, both products of Hayashibara Biochemical Laboratories, Inc., Okayama, Japan, and reacted at pH6.0 and 45° C. for 24 hours. The reaction mixtures were heated at 95° C. for 10 minutes, cooled, added with 10 units/g starch solid of glucoamylase and reacted at pH5.0 for 10 hours. The reaction mixtures were analyzed on high-performance liquid chromatography to determine the trehalose contents (%) in the resultant saccharides. As control, fresh preparations of the same those with relatively low liquefaction degrees are preferred; desirably, those with DE lower than 15, more desirably, with DE lower than 10. As to the enzymes therefor, it was found that combination of non-reducing saccharide-forming enzyme, trehalose-releasing enzyme and starch debranching enzyme and/or cyclomaltodextrin glucanotransferase was very favorable in industrial-scale production of trehalose from starch rather than that of non-reducing saccharide-forming enzyme and trehalose-releasing enzyme because the former combination increased yields for trehalose from starch by about 2–4 folds.

The following Examples A are to illustrate the processes to produce non-reducing saccharide, less reducing saccharide containing the same and trehalose which are all according to the present invention, while Examples B are to illustrate compositions which contain the non-reducing saccharide, less reducing saccharides and/or trehalose.

EXAMPLE A-1

Potato starch in about 20% suspension was added with 0.3% oxalic acid, autoclaved, cooled and neutralized with calcium carbonate to pH6.5 to obtain a liquefied starch solution with about DE12. The liquefied starch solution was added with 2 units/g starch solid of a purified non-reducing saccharide-forming enzyme obtained by the method in Experiment 2 and 300 units/g starch solid of the isoamylase commercialized by Hayashibara Biochemical Laboratories, Inc., Okayama, Japan, and reacted at 45° C. for 24 hours.

The reaction mixture was heated to 95° C. to inactivate the enzymes, cooled and filtered and the filtrate was decolored with activated carbon, deionized with ion exchanges of H- and OH-forms for purification and concentrated to obtain a syrup product, concentration of about 70%, at the yield of about 90% on dry solid basis. The product is a less reducing saccharide containing alpha-glycosyl trehaloses, DE of about 8, which can be favorably used as sweetener, taste improving agent, quality improving agent, stabilizer and shape imparting agent in a variety of compositions including food products, cosmetics and medicines because it bears a mild and gentle sweetness, a relatively low viscosity and an appropriate moisture retainability.

EXAMPLE A-2

Tapioca starch in about 25% suspension was added with 0.2% against starch solid of "NEO-SPITASE", an alpha-amylase commercialized by Nagase Biochemicals, Kyoto, Japan, reacted at 85–90° C. for about 20 minutes, autoclaved at 120° C. and immediately cooled to obtain a liquefied starch solution of about DE4 which was then added with 5 units/g starch solid of a purified non-reducing saccharide-forming enzyme obtained by the method in Experiment 9 along with 100 units/g starch solid of pullulanase and 5 units/g starch solid of maltotetraose-forming enzyme, both products of Hayashibara Biochemical Laboratories, Inc., Okayama, Japan, and reacted at pH6.5 and 40° C. for 36 hours. The reaction mixture was heated to inactivate the enzymes, purified and concentrated similarly as in Example A-1 to about 60%. To elevate the non-reducing saccharide content in the resultant concentrate as starting saccharide liquid, a column chromatography on "XT-1016", a strongly-acidic cation exchange of sodium form, was conducted. The ion exchange resin was packed in 4 jacketed-stainless steel columns, inner diameter of 5.4 cm each, which were then cascaded to give a total length of 20 m. While keeping the temperature inside the columns at 55° C., they were added with 5 v/v % saccharide liquid against the resin and injected with 55° C. water at SV0.2, followed by recovering fractions which contained non-reducing saccharides with glucose polymerization degrees of 4–6. The fractions were purified, concentrated, dried in vacuo and pulverized to obtain a powder product with a high non-reducing saccharide content at the yield of about 63% on dry solid basis. The product is a non-reducing saccharide containing alpha-glycosyl trehaloses, DE of 5.4, which can be favorably used as sweetener, taste improving agent, quality improving agent, stabilizer and shape imparting agent in a variety of compositions including food products, cosmetics and medicines because it bears a mild and gentle sweetness, a relatively low viscosity and an appropriate moisture retainability.

EXAMPLE A-3

Cornstarch in about 30% suspension was added with 0.1% calcium carbonate, adjusted to pH6.5, added with 0.3% against starch solid of "TERMAMYL 60L", an alpha-amylase commercialized by Novo Industri AS, Copenhagen, Denmark, reacted at 95° C. for 15 minutes, autoclaved at 120° C. and immediately cooled to obtain a liquefied starch solution with about DE4 which was then added with 4 units/g starch solid of a purified non-reducing saccharide-forming enzyme obtained by the method in Experiment 2 along with 300 units/g starch solid of isoamylase and 5 units/g starch solid of cyclomaltodextrin glucanotransferase, both products of Hayashibara Biochemical Laboratories, Inc., Okayama, Japan, and reacted at pH6.3 and 45° C. for 48 hours. The reaction mixture was kept at 95° C. for 10 minutes, cooled, added with 10 units/g starch solid of beta-amylase and further reacted at pH5.5 and 55° C. for 16 hours. The reaction mixture was heated to inactivate the enzyme, decolored and deionized in conventional manner for purification and concentrated to obtain a syrup product, concentration of about 70%, at the yield of about 90% on dry solid basis. The product is a less reducing saccharide containing non-reducing saccharides such as alpha-glycosyl trehaloses and alpha-glycosyl alpha-glycosides which can be favorably used as sweetener, taste improving agent, quality improving agent, stabilizer and shape imparting agent in a variety of compositions including food products, cosmetics and medicines because it bears a mild and gentle sweetness, a relatively low viscosity and an appropriate moisture retainability.

EXAMPLE A-4

A syrup product obtained by the method in Example A-3 was diluted to about 55% and subjected to column chromatography on strongly-acidic cation exchange of salt form in accordance with the method in Example A-2 to increase the content for non-reducing saccharides and fractions containing non-reducing saccharides with glucose polymerization degrees of 3–6 were recovered, purified, concentrated and spray-dried to obtain a powder product with a high non-reducing saccharide content at the yield of about 38% on dry solid basis. The product is a less reducing saccharide containing large amounts of non-reducing saccharides such as alpha-glycosyl trehaloses and alpha-glycosyl alpha-glycosides, DE of 8, which can be favorably used as sweetener, taste improving agent, quality improving agent, stabilizer and shape imparting agent in a variety of compositions including food products, cosmetics and medicines because it bears a mild and gentle sweetness, a relatively low viscosity and an appropriate moisture retain-ability.

EXAMPLE A-5

Cornstarch in about 30% suspension was subjected to alpha-amylase in accordance with the method in Example A-3 into a liquefied starch solution with DE4 which was then added with 5 units/g starch solid of a purified non-reducing saccharide-forming enzyme obtained by the method in Experiment 15 and 500 units/g starch solid of isoamylase and reacted at pH6.0 and 40° C. for 48 hours. The reaction mixture contained 76.3% trehalose with respect to saccharide composition. The reaction mixture was then heated to inactivate the enzymes, decolored and deionized in conventional manner for purification, concentrated to about 85%, placed in a crystallizer, crystallized under stirring and gradually cooling conditions, distributed in plastic baths, allowed to standing at ambient temperature for 2 days and aged to complete crystallization to obtain solid products in block form. The products were then subjected to cutting machine to obtain a powder product of crystalline trehalose hydrate at the yield of 92% on dry solid basis. The product can be favorably used as sweetener, taste improving agent, quality improving agent, stabilizer and shape imparting agent in a variety of compositions including food products, cosmetics and medicines because it is substantially free of hygroscopicity and easily handleable.

EXAMPLE A-6

Tapioca starch in about 30% suspension was subjected to alpha-amylase in accordance with the method in Example A-2 to obtain a liquefied starch solution with DE5 which was then added with 3 units/g starch solid of a purified non-reducing saccharide-forming enzyme obtained by the method in Experiment 10 and 5 units/g starch solid of a purified trehalose-releasing enzyme obtained by the method in Experiment 23 along with 200 units/g starch solid of pullulanase and 3 units/g starch solid of cyclomaltodextrin glucanotransferase and reacted at pH6.0 and 45° C. for 48 hours. The reaction mixture contained 84.7% trehalose on dry solid basis. The reaction mixture was then heated to inactivate the enzymes, decolored and deionized for purification in conventional manner and crystallized in continuous manner while concentrating, and the crystals in the resultant massecuite were separated by basket-type centrifuge and sprayed with a minimum amount of water for washing, thus obtaining a high-purity crystalline trehalose hydrate at the yield of about 55% on dry solid basis. The product, a crystalline trehalose hydrate with an extremely high purity, can be favorably used in a variety of compositions including food products, cosmetics and medicines, as well as reagent and material for industrial and chemical uses.

EXAMPLE A-7

A heat-inactivated reaction mixture obtained by the method in Example A-6 was added with 10 units/g substrate solid of glucoamylase and reacted at pH5.0 and 50° C. for 10 hours. The reaction mixture was heated to inactivate the enzyme, decolored and deionized for purification in conventional manner, concentrated to about 70%, placed in crystallizer and crystallized under stirring and gradually cooling conditions to obtain a massecuite with a crystallization degree of about 40%. The massecuite was then sprayed at 150 kg/cm$^2$ through a high-pressure nozzle provided at the top of a drying tower, while supplying downwards 85° C. air from the top of the drying tower and collecting the resultant crystalline powder on a conveyer of metal net provided at the bottom of the drying tower. The crystalline powder was gradually moved and transferred outside the drying tower while supplying 45° C. air upwardly through the conveyer. The crystalline powder was placed in ageing tower where the powder was aged for 10 hours in a stream of warmed air to complete crystallization and drying, thus obtaining a crystalline trehalose hydrate product at the yield of about 87% against material starch solid. The product can be favorably used as sweetener, taste improving agent, quality improving agent, stabilizer and shape imparting agent in a variety of compositions including food products, cosmetics and medicines because it is substantially free of hygroscopicity and easily handleable.

EXAMPLE A-8

A mutant of Rhizobium species M-11 (FERM BP-4130) was cultivated for about 70 hours in accordance with the method in Experiment 1. The culture was passed through SF membrane to remove the cells and the filtrate, about 100 liters, was then passed through UF membrane to obtain 5 liters of a concentrate which contained about 410 units/ml non-reducing saccharide-forming enzyme and about 490 units/ml trehalose-releasing enzyme. Cornstarch in about 33% suspension was subjected to alpha-amylase in accordance with the method in Example A-3 to obtain a liquefied starch solution with about DE4 which was then added with 0.02 ml/g starch solid of the above concentrate, 500 units/g starch solid of isoamylase and 5 units/g starch solid of cyclomaltodextrin glucanotransferase and reacted at pH6.2 and 40° C. for 48 hours. The reaction mixture was heated to inactivate the enzymes, added with 10 units/g substrate solid of glucoamylase and further reacted at pH5.0 and 50° C. for 10 hours. The reaction mixture contained 85.6% trehalose on dry solid basis. The reaction mixture was then heated to inactivate the enzyme, decolored and deionized for purification in conventional manner and crystallized in continuous manner while concentrating, and the crystals in the resultant massecuite were separated with basket-type centrifuge and sprayed with a minimum amount of water for washing, thus obtaining a high-purity crystalline trehalose hydrate at the yield of 64% on dry solid basis. The product, a crystalline trehalose hydrate with an extremely high purity, can be favorably used in a variety of compositions including food products, cosmetics and medicines, as well as reagent and material for industrial and chemical uses.

EXAMPLE A-9

A reaction mixture obtained by the method in Example A-8 was heated to inactive enzymes, decolored and deionized for purification in conventional manner and concentrated to obtain a 55% syrup product. The product was applied as starting saccharide liquid to column chromatography on "DOWEX 99", a strongly-acidic cation exchange of calcium form, crosslinkage degree of 6%, commercialized by The Dow Chemical Co., Midland, Mich., USA, to elevate the content for trehalose, followed by recovering trehalose-rich fractions. The fractions were then decolored and deionized in conventional manner, placed in evaporator and boiled in vacuo into a syrup with a moisture content of about 3.0%. The syrup was placed in crystallizer, added with 1% anhydrous crystalline trehalose as seed crystal against syrup solid, crystallized at 120° C. while stirring, distributed in aluminum baths and aged at 100° C. for 6 hours to obtain solid products in block form. The solid products were then subjected to cutting machine and dried while fluidizing to obtain a powder product of anhydrous crystalline trehalose with a moisture content of about 0.3% at the yield of about 75% against the solid in the trehalose-rich fractions. The product can be favorably used as desiccant for hydrous substances such as food products, cosmetics, medicines and their materials and intermediates, as well as sweetener with an gentle sweetness in a variety of compositions including food products, cosmetics and medicines.

EXAMPLE B-1

Sweetener

One part by weight of a crystalline trehalose hydrate powder obtained by the method in Example A-7 was mixed to homogeneity with 0.01 part by weight of "ALPHA G SWEET", an alpha-glycosyl stevioside commercialized by Toyo Sugar Refining Co., Ltd., Tokyo, Japan, and 0.01 part by weight of "ASPARTAME", an L-aspartyl-L-phenylalanine methyl ester commercialized by Ajinomoto Inc., Tokyo, Japan, and the mixture was fed to granulater to obtain a granular product of sweetener. The product has a superior quality for sweetness and a sweetening power about 2-fold stronger than that of sucrose and its calorie is about one half of that of sucrose per sweetening power. Since the product is superior in stability and free of decomposition of the ingredients which exhibit high sweetening powers, it is suitable as low-calorie sweetener to sweeten low-calorie food products for persons with diabetes or obesity whose calorie intakes are restricted. Further the product is suitable to sweeten food products which are suppressive on dental caries because it induces less formation of acids and insoluble glucans by dental caries-causative micro-organisms.

EXAMPLE B-2

Hard candy

One hundred parts by weight of 55% sucrose solution was mixed with 30 parts by weight of a syrup containing non-reducing saccharides obtained by the method in Example A-1 while heating, concentrated by heating in vacuo to a moisture content lower than 2%, admixed with one part by weight of citric acid and appropriate amounts of lemon flavor and coloring agent and shaped in conventional manner to obtain products. The products are high-quality hard candies which are crisp, superior in taste and free of crystallization of sucrose and deformation.

EXAMPLE B-3

Chocolate

Forty parts by weight of cacao paste, 10 parts by weight of cacao butter, 30 parts by weight of sucrose, 20 parts by weight of a high-purity crystalline trehalose hydrate obtained by the method in Example A-8 were mixed, fed to refiner to reduce particle sizes and kneaded in conche at 50° C. for 2 days. During the kneading, 0.5 parts by weight of lecithin was added and sufficiently dispersed to homogeneity. The resultant was adjusted to 31° C. with thermocontroller, distributed in molds immediately before solidification of the butter, deaerated with vibrator and passed through 10° C. cooling tunnel over 20 minutes for solidification. The contents were taken out from the molds and packaged to obtain products. The products are free of hygroscopicity but have a superior color, gloss and texture and smoothly dissolves in the mouth to give a gentle sweetness and a mild flavor and taste.

EXAMPLE B-4

Chewing gum

Three parts by weight of gum base was softened by melting while heating, added with 4 parts by weight of sucrose and 3 parts by weight of a crystalline trehalose hydrate powder obtained by the method in Example A-5, mixed with appropriate amounts of flavoring and coloring agents, kneaded with roller in conventional manner, shaped and packaged to obtain a product. The product is a chewing gum with a superior texture, flavor and taste.

EXAMPLE B-5

Sweetened condensed milk

In 100 parts by weight of fresh milk was dissolved 3 parts by weight of a syrup containing non-reducing saccharides obtained by the method in Example A-3 and one part by weight of sucrose and the mixture was pasteurized by heating on plate heater, concentrated to 70% and sterilely canned to obtain a products. The product, which has a mild sweetness and a superior flavor and taste, can be favorably used as seasoning in infants' foods, fruits, coffee, cocoa and tea.

EXAMPLE B-6

Beverage containing lactic acid bacteria

One hundred and seventy-five parts by weight of defatted milk, 8 parts by weight of a powder with high non-reducing saccharide content obtained by the method in Example A-2 and 50 parts by weight of a powder with high lactosucrose content as disclosed in Japanese Patent Kokai No. 281,795/92 were dissolved in 1,200 parts by weight of water, pasteurized at 65° C. for 30 minutes, cooled to 40° C., added with 30 parts by weight of starter and cultivated at 37° C. for 8 hours in conventional manner to obtain a beverage which contained lactic acid bacteria. The product is superior in taste and flavor. The oligosaccharides in the product stably maintain lactic acid bacteria and stimulate the growth of bifidobacteria.

EXAMPLE B-7

Powdered juice

Thirty three parts by weight of orange juice powder prepared by spray drying was mixed by stirring to homogeneity with 50 parts by weight of a high-purity crystalline trehalose hydrate obtained by the method in Example A-6, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan and an appropriate amount of powdered flavoring agent, cut into fine powder, fed to fluidized-bed granulator, sprayed at an exhausting temperature of 40° C. with a syrup as binder which had been obtained by purifying and concentrating a high-trehalose content reaction mixture obtained by the method in Example A-6, granulated for 30 minutes, divided into prescribed amounts and packaged to obtain a product. The product is a powdered juice with a fruit juice content of about 30%. The product was free of unpleasant taste and odor and stable over an extended time period.

EXAMPLE B-8

Custard cream

One hundred parts by weight of cornstarch, 100 parts by weight of a syrup containing non-reducing saccharides obtained by the method in Example A-1, 80 parts by weight of maltose, 20 parts by weight of sucrose and one part by weight of sodium chloride were mixed to homogeneity, added with 280 parts by weight of egg, stirred, gradually added with 1,000 parts by weight of boiling milk, further stirred on slow fire till the cornstarch completely gelatinized and the content gave a semitransparency, after which the resultant was cooled, added with an appropriate amount of vanilla flavor, divided into prescribed portions and packaged to obtain a product. The product has a smooth gloss, mild sweetness and superior taste.

EXAMPLE B-9

"Uiro-no-moto"

Ninety parts by weight of rice powder was mixed to homogeneity with 20 parts by weight of cornstarch, 40 parts by weight of sucrose, 80 parts by weight of a crystalline trehalose hydrate powder obtained by the method in Example A-5 and 4 parts by weight of pullulan to obtain "uiro-no-moto". The uiro-no-moto was then kneaded to homogeneity with appropriate amounts of "matcha" or powdered green tea in water, placed in vessels and steamed for 60 minutes to obtain "matcha-uiro". The product is superior in gloss, texture, taste and flavor. The product has an extended shelf life because retrogradation of starch is effectively suppressed.

EXAMPLE B-10

"An (bean paste)"

In conventional manner, 10 parts by weight of adzuki bean as material was added with water and boiled and the astringency, harshness and water-soluble concomitants were removed to obtain about 21 parts by weight of a lumpy raw adzuki bean paste. The raw bean paste was then added with 14 parts by weight of sucrose, 5 parts by weight of a syrup containing non-reducing saccharides obtained by the method in Example A-3 and 4 parts by weight of water, boiled, further added with a small amount of salad oil and kneaded with care of not disrupting the granules of adzuki beans, thus obtaining about 35 parts by weight of a bean paste product. The product, which is free of discoloration and superior in texture, taste and flavor, is suitable as material for "anpan", "manju", "dango", "monaka" and frozen desserts.

EXAMPLE B-11

Bun

In conventional manner, 100 parts by weight of wheat flour, 2 parts by weight of yeast, 5 parts by weight of sucrose, one part by weight of a powder containing non-reducing saccharides obtained by the method in Example A-4 and 0.1 part by weight of inorganic foods were kneaded in water, fermented at 26° C. for 2 hours, aged for 30 minutes and baked. The product is a high-quality bun with a superior color and texture, an appropriate elasticity and a mild sweetness.

EXAMPLE B-12

Ham

One thousand parts by weight of upper parts of pig leg was uniformly salted with 15 parts by weight of sodium chloride and 3 parts by weight of potassium nitrate and piled up in a chilled place for one day. The resultant was soaked in a chilled place for 7 days in a salting solution consisting of 500 parts by weight of water, 100 parts by weight of sodium chloride, 3 parts by weight of potassium nitrate, 40 parts by weight of a powder containing non-reducing saccharides obtained by the method in Example A-4 and spices, washed with chilled water, bound, smoked, cooked, cooled and packaged to obtain a product. The product is a high-quality ham with a superior color, taste and flavor.

EXAMPLE 13

Powdered peptide

One part by weight of "HIMUTE S", a soybean peptide in 40% solution directed to use in food products commercialized by Fuji Oil Co., Ltd., Osaka, Japan, was mixed with 2 parts by weight of a high-purity crystalline trehalose hydrate obtained by the method in Example A-6, placed in plastic baths, dried at 50° C. in vacuo and cut to obtain a powder product of peptide. The product, which is superior in taste and flavor, can be favorably used as material in confectioneries such as mixes and ice desserts, as well as babies' foods and nutriment for therapeutic uses including oral and parenteral liquid foods.

EXAMPLE B-14

Powdered miso

One part by weight of red miso was mixed with 3 parts by weight of an anhydrous crystalline trehalose powder obtained by the method in Example A-9, poured in a plurality of concaves on metal plate, allowed to stand at ambient temperature overnight for solidification and put off from the plate to obtain miso solids, about 4 g each, which were then fed to cutting machine into powder. The product can be favorably used as seasoning in convenient Chinese-style noodles and "suimono", a type of clear soup. While the miso solids can be used intact as confectionery, as well as solid seasoning.

EXAMPLE B-15

Powdered egg york

Raw egg york was pasteurized at 60–64° C. on plate heater and the obtained egg york liquid was mixed with 4 parts by weight of an anhydrous crystalline trehalose powder obtained by the method in example A-9 against one part by weight of the egg york liquid, distributed in baths and allowed to stand overnight to convert the trehalose into crystalline hydrate form, thus obtaining solid products of block form. The solid products were then fed to cutting machine to obtain a powdered egg york. The product can be favorably used as material for confectioneries such as mixes, ice desserts and emulsifier, as well as babies' food and nutriment for therapeutic uses including oral and parenteral liquid foods.

EXAMPLE B-16

Cosmetic cream

Two parts by weight of polyoxyethylene glycol monostearate, 5 parts by weight of self-emulsifying glycerin monosterate, 2 parts by weight of a powder with high non-reducing saccharide content obtained by the method in Example A-2, one part by weight of alpha-glycosyl rutin, one part by weight of liquid paraffin, 10 parts by weight of glyceryl trioctanate and an appropriate amount of antiseptic were dissolved by heating in conventional manner, added with 2 parts by weight of L-lactic acid, 5 parts by weight of 1,3-butylene glycol and 66 parts by weight of refined water, fed to homogenizer for emulsification and admixed by stirring with an appropriate amount of flavoring agent to obtain a cream product. The product, which bears anti-oxidization activity and elevated stability, can be favorably used as high-quality anti-suntan agent, skin-refining agent and skin-whitening agent.

EXAMPLE B-17

Hair rinse

One part by weight of trehalose obtained by the method in Example A-6, 2 parts by weight of alpha-glucosyl-L-ascorbic acid commercialized by Hayashibara Biochemical Laboratories, Inc., Okayama, Japan, 2 parts by "ALPHA G RUTIN", an enzyme-treated rutin commercialized by Toyo Sugar Refining Co., Ltd., Tokyo, Japan, 2 parts by weight of distearic methyl ammonium chloride, 2 parts by cetanol, 2 parts by weight of silicone oil, 1 part by weight of polyoxyethylene oleil alcohol ether and an appropriate amount of flavoring agent were dissolved while heating, added with a mixture of 3 parts by weight of 1,3-butylene glycol, 89 parts by weight of refined water and an appropriate amount of antiseptic while stirring, cooled and allowed to standing to obtain a hair rinse. The product with alpha-glucosyl-L-ascorbic acid and enzyme-treated rutin can be favorably used to stimulate the generation and growth of hair in humans and animals, as well as to treat and prevent scurf, itching and fallen hair.

EXAMPLE B-18

Milky lotion

A milky lotion was prepared in conventional manner with the following formulation (parts by weight):

| | |
|---|---|
| POE (20) cetyl alcohol ether | 1 |
| "SILICONE KF96" commercialized by the Shin-etsu Chemical Industry Co., Ltd., Tokyo, Japan | 2 |
| Liquid paraffin | 5 |
| Propylene glycol | 1 |
| Glycerin | 1 |
| Trehalose obtained in Example A-7 | 1 |
| Ethyl alcohol | 15 |
| Caboxyvinyl polymer | 0.3 |
| Hydroxypropyl cellulose | 0.1 |
| 2-Aminomethyl propanol | 0.1 |
| POE in castor oil | 0.1 |
| Alpha-glucosyl-L-ascorbic acid | 1 |
| Red Pigment No. 106 | 0.0001 |
| Antiseptic | trace |
| Flavoring agent | 0.1 |
| Distilled water | 70 |

The product with alpha-glucosyl-L-ascorbic acid was superior in skin-refining ability, stability and flavor-retaining ability.

EXAMPLE B-19

Face lotion

A face lotion was prepared in conventional manner with the following formulation (parts by weight):

| | |
|---|---|
| Sorbitol | 2 |
| Trehalose obtained in Example A-8 | 0.5 |
| Placeta liquid | 0.5 |
| Alpha-glucosyl-L-ascorbic acid | 0.5 |
| Dimethyl stearylamine oxide | 0.05 |
| Sodium laurate | 0.01 |
| Ethyl alcohol | 20 |
| Antiseptic | trace |
| Flavoring agent | trace |
| Distilled water | 75 |

The product with alpha-glucosyl-L-ascorbic acid was superior in skin-refining ability, stabilty and safeness.

EXAMPLE B-20
Powdered ginseng extract

One half part by weight of ginseng extract was kneaded together with 1.5 parts by weight of an anhydrous crystalline trehalose powder obtained by the method in Example A-9, placed in baths and allowed to stand for 2 days to convert the trehalose into crystalline hydrate form, thus obtaining solid products in block form. The solid products were then fed to cutting machine for pulverization and sieved to obtain a powdered ginseng extract. The powder was fed to granulator together with appropriate amounts of vitamin B1 and vitamin B2, both in powder, into a granular ginseng extract containing vitamins. The product can be favorably used as tonic. Further the product can be also used as hair restorer.

EXAMPLE B-21
Solid agent

A natural human interferon-alpha preparation commercialized by Hayashibara Biochemical Laboratories, Inc., Okayama, Japan, was applied to an immobilized anti-human interferon-alpha antibody column in conventional manner so as to adsorb the human interferon-alpha and also to pass through the bovine serum albumin as stabilizer, and the adsorbed natural human interferon-alpha was eluted with a physiological saline containing 5% high-purity crystalline trehalose hydrate obtained by the method in Example A-6 while changing the pH level in the saline. The obtained liquid was filtered through membrane, added with about 20-fold amount of "FINETOSE", an anhydrous crystalline maltose commercialized by Hayashibara Biochemical Laboratories, Inc., Okayama, Japan, for desiccation, pulverized and fed to tabletting machine to obtain tablets, about 200 mg each, which contained about 150 units of natural human interferon-alpha per tablet. The product can be favorably used as sublingual tablet in the treatment of viral diseases, allergic diseases, rheumatism, diabetes and malignant tumors where the product is orally administered in a dose of 1–10 tablets/day/adult. Especially the product can be favorably used in the treatment of AIDS and hepatitis whose incidences have been rapidly increasing in these years. The product retains its activities over an extended time period even when allowed to standing at ambient temperature because both non-reducing saccharide according to the present invention and anhydrous crystalline maltose act as stabilizers.

EXAMPLE B-22
Sugar-coated tablet

Non-coated tablets as core material, 150 mg each, were coated with an undercoating liquid consisting of 40 parts by weight of a high-purity crystalline trehalose hydrate obtained by the method in Example A-8, 2 parts by weight of pullulan with an averaged molecular weight of 200,000 daltons, 30 parts by weight of water, 25 parts by weight of talc and 3 parts by weight of titanium oxide to give about 230 mg per tablet, further coated with a final coating liquid consisting of 65 parts by weight of the same crystalline trehalose hydrate, one part by weight of pullulan and 34 parts by weight of water and polished with liquid wax to obtain sugar-coated tablets with superior glossy appearance. The product has a superior shock resistance and retains a high-quality over an extended time period.

EXAMPLE B-23
Dentifrice

Formulation (parts by weight):

| | |
|---|---|
| Calcium hydrogen phosphate | 45.0 |
| Pullulan | 2.95 |
| Sodium lauryl sulfate | 1.5 |
| Glycerin | 20.0 |
| Polyoxyethylene sorbitan laurate | 0.5 |
| Antiseptic | 0.05 |
| Crystalline trehalose hydrate powder obtained by the method in Example A-5 | 12.0 |
| Maltitol | 5.0 |
| Water | 13.0 |

The above described materials were mixed in conventional manner to obtain a dentifrice. The product, which has an appropriate sweetness, is suitable as children' dentifrice.

EXAMPLE B-24
Solid agent for liquid food

A composition consisting of 500 parts by weight of a crystalline trehalose hydrate powder prepared by the method in Example A-7, 270 parts by weight of powdered egg york, 4.4 parts by weight of sodium chloride, 1.8 parts by weight of potassium chloride, 4 parts by weight of magnesium sulfate, 0.01 part by weight of thiamin, 0.1 part by weight of sodium ascorbate, 0.6 parts by weight of vitamin E acetate and 0.04 parts by weight of nicotinamide was divided into 25 g aliquots which were then packed in moisture-proof laminated bags and heat-sealed to obtain a product. One bag of the product is dissolved in about 150–300 ml water into a liquid food which is then administered in the oral or nasal cavity, stomach or intestine for energy supplementation to living bodies.

EXAMPLE B-25
Infusion agent

A high-purity crystalline trehalose hydrate produced by the method in Example A-8 was dissolved in water to about 10 w/v %, passed through membrane to remove pyrogens, sterilely bottled in plastic bottles and sealed in conventional manner. The product is a stable infusion agent which is free of alteration in time course and suitable for intravenous and intraperitoneal administration. The product is isotonic at 10 w/v % to blood and therefore capable of supplementing at the concentration 2-fold more energy than in case of using glucose.

EXAMPLE B-26
Infusion agent

A high-purity crystalline trehalose hydrate obtained by the method in Example A-8 and an amino acid mixture with the below described formulation were mixed and dissolved in water to 5 w/v % and 30 w/v % respectively, purified similarly as in EXAMPLE B-25 to remove pyrogens, distributed in plastic bags and sealed.

Formulation of the amino acid mixture (mg/100 ml):

| | |
|---|---|
| L-Isoleucine | 180 |
| L-Leucine | 410 |
| L-Lysine hydrochloride | 620 |
| L-Methionine | 240 |
| L-Phenylalanine | 290 |
| L-Threonine | 180 |
| L-Tryptophane | 60 |
| L-Valine | 200 |
| L-Arginine hydrochloride | 270 |
| L-Histidine hydrochloride | 130 |
| Glycine | 340 |

The product is a stable infusion agent which is free of alteration in time course and favorably administrable through intravenous and intraperitoneal routes because trehalose exhibits no reducing power even in this type of composition of saccharide and amino acid. The procut can be favorably used to supplement both energy and amino acids to living bodies.

EXAMPLE B-27
Ointment for treating external injury

Two hundred parts by weight of a crystalline trehalose hydrate powder prepared by the method in Example A-5 and 300 parts by weight of maltose were first admixed with 3 parts by weight of iodine in 50 parts by weight of methanol, then with 200 parts by weight of 10 w/v % aqueous pullulan solution, thus obtaining an ointment with an appropriate extensibility and adhesiveness. The use of the product superiorly heals external injuries in a shortened treatment period because the iodine and trehalose in the product act as disinfectant and energy supplementing agent to viable cells respectively.

Effect of the Invention

As obvious from the above explanation, in the production of non-reducing saccharides with trehalose structures such as alpha-glycosyl trehaloses and alpha-glycosyl alpha-glycosides and less reducing saccharides containing the same from starch, combination of non-reducing saccharide-forming enzyme and starch debranching enzyme and/or cyclomaltodextrin glucanotransferase improves the yields for non-reducing saccharides from liquefied starches in solution, as well as facilitating the industrial-scale production of relatively small less reducing saccharides with decreased viscosity and superior handleability. Further in the production of trehalose from starch, combination of non-reducing saccharide-forming enzyme, trehalose-releasing enzyme and either of both of starch debranching enzyme and cyclomaltodextrin glucanotransferase greatly improves the yield for trehalose from starch and facilitates its industrial-scale production. The non-reducing saccharides including alpha-glycosyl trehalose and alpha-glycosyl alpha-glycoside and trehalose and less reducing saccharides containing the same bear a superior stability and a high-quality, mild sweetness. Still further they are digested and absorbed as calorie source when orally intaken. Trehalose would also find parenteral uses where it is readily metabolized and assimilated. Thus the non-reducing saccharides and less reducing saccharides containing the same both according to the present invention can be favorably used as sweeteners, taste improving agents, quality improving agents, stabilizers and shape imparting agents in a variety of compositions including food products, cosmetics and medicines.

The present invention would open an entirely novel way to industrial-scale production to provide at low cost desired amounts of non-reducing saccharides and less reducing saccharides containing the same, which have been in great demand but not easily obtained, from starch as cheap and indefinite source. Thus the effect of the present invention would come up to agricultural, fishery and stockbleeding and chemical industries as well as to food, cosmetic and pharmaceutical industries and its industrial significance would be inestimatable.

We claim:

1. A non-reducing saccharide having a trehalose structure wherein at least one molecule of glucose is attached to each of the glucose molecules making up the trehalose structure which is obtainable by subjecting a solution of liquified starch to a non-reducing saccharide-forming enzyme, a starch-debranching enzyme, and cyclomaltodextrin glucanotransferase, or to a non-reducing saccharide-forming enzyme, a trehalose-releasing enzyme, a starch-debranching enzyme, and cyclomaltodextrin glucanotransferase; and collecting the produced non-reducing saccharide.

2. The non-reducing saccharide of claim 1, wherein said solution is of 10 w/w % or more starch which has been liquefied to a DE lower than 15.

3. The non-reducing saccharide of claim 1, wherein said solution is created with said starch-debranching enzyme or cyclomaltodextrin glucanotransferase and an alpha-amylase which forms an oligosaccharide with a glucose polymerization degree of 3 or higher.

4. A saccharide composition which comprises the non-reducing saccharide of claim 1 and others saccharides.

5. A process for producing a non-reducing saccharide having a trehalose structure or a saccharide composition containing the same, wherein said non-reducing saccharide has at least one molecule of glucose attached to each of the glucose molecules making up the trehalose structure, said process comprising:

subjecting a solution of liquified starch to a non-reducing saccharide-forming enzyme, a starch-debranching enzyme, and cyclomaltodextrin glucanotransferase or to a non-reducing saccharide-forming enzyme, a trehalose-releasing enzyme and a starch-debranching enzyme, and cyclomaltodextrin glucanotransferase to form such non-reducing saccharide; and collecting the non-reducing saccharide or a saccharide composition containing the non-reducing saccharide.

6. The process of claim 5, wherein said solution is of 10 w/w % or more starch which has been liquefied to a DE lower than 15.

7. A process for producing a non-reducing saccharide having a trehalose structure or a saccharide composition containing the same, said non-reducing saccharide having at least one molecule of glucose attached to each of the glucose molecules making up the trehalose structure, such process comprising:

subjecting a solution of liquified starch to a non-reducing saccharide-forming enzyme, a starch-debranching enzyme, and cyclomaltodextrin glucanotransferase or to a non-reducing saccharide-forming enzyme, a trehalose-releasing enzyme, and a starch-debranching enzyme and cyclomaltodextrin glucanotransferase;

optionally contacting the resultant with beta-amylase, glucoamylase or alpha-glucosidase to form a solution which contains said non-reducing saccharide and contaminant saccharides;

applying the solution to column chromatography; and collecting a fraction which comprises said non-reducing saccharide or comprises said non-reducing saccharide and other saccharides.

8. The process of claim 7, wherein said column chromatography uses a strongly-acidic cation exchange in salt form.

9. In a method for producing a non-reducing saccharide having a trehalose structure wherein at least one molecule of glucose is attached to each of the glucose molecules making up the trehalose structure, wherein a solution of liquified starch is subjected either to a non-reducing saccharide-forming enzyme or to a non-reducing saccharide-forming enzyme and a trehalose-releasing enzyme, the improvement comprising elevating the yield of such non-reducing saccharide, comprising allowing a starch-debranching enzyme and cyclomaltodextrin glucanotransferase and either or both of the non-reducing saccharide enzyme and the trehalose-releasing enzyme to act on said solution.

10. A composition, which contains the non-reducing saccharide of claim 1.

11. The composition of claim 10, wherein the content for the non-reducing saccharide has been increased by column chromatography.

12. The composition of claim 10, which is a food product, cosmetic or medicine.

13. A process for producing a food comprising:

subjecting a solution of liquified starch to a non-reducing saccharide-forming enzyme, a starch-debranching enzyme, and cyclomaltodextrin glucanotransferase, or to a non-reducing saccharide-forming enzyme, a trehalose-releasing enzyme, a starch-debranching enzyme and cyclomaltodextrin glucanotransferase to form a non-reducing saccharide having a trehalose structure wherein at least one molecule of glucose is attached to each of the glucose molecules making up the trehalose structure;

collecting the non-reducing saccharide or a saccharide composition containing the non-reducing saccharide, and incorporating the non-reducing saccharide or the saccharide composition into a food material.

14. A process for producing a cosmetic comprising:

subjecting a solution of liquified starch to a non-reducing saccharide-forming enzyme, a starch-debranching enzyme, and cyclomaltodextrin glucanotransferase, or to a non-reducing saccharide-forming enzyme, a trehalose-releasing enzyme, a starch-debranching enzyme and cyclomaltodextrin glucanotransferase to form a non-reducing saccharide having a trehalose structure wherein at least one molecule of glucose is attached to each of the glucose molecules making up the trehalose structure;

collecting the non-reducing saccharide or a saccharide composition containing the non-reducing saccharide, and incorporating the non-reducing saccharide or a saccharide composition containing the non-reducing saccharide into a cosmetically acceptable material.

15. A process for producing a pharmaceutical composition comprising:

subjecting a solution of liquified starch to a non-reducing saccharide-forming enzyme, a starch-debranching enzyme, and cyclomaltodextrin glucanotransferase, or to a non-reducing saccharide-forming enzyme, a trehalose-releasing enzyme, a starch-debranching enzyme and cyclomaltodextrin glucanotransferase to form a non-reducing saccharide having a trehalose structure wherein at least one molecule of glucose is attached to each of the glucose molecules making up the trehalose structure;

collecting the non-reducing saccharide or a saccharide composition containing the non-reducing saccharide, and incorporating the non-reducing saccharide or a saccharide composition containing the non-reducing saccharide into a pharmaceutically acceptable material.

16. The process according to claim 5 wherein said saccharide composition comprises said non-reducing saccharide and at least one member selected from the group consisting of non-reducing saccharides bearing at the end a trehalose structure, non-reducing saccharides bearing within the molecule a trehalose structure, and trehalose.

17. The process of claim 16 wherein said trehalose is crystalline trehalose hydrate or anhydrous crystalline trehalose.

18. The process of claim 7 wherein said saccharide composition comprises said non-reducing saccharide and at least one member selected from the group consisting of non-reducing saccharides bearing at the end a trehalose structure and trehalose.

19. The process of claim 18 wherein said trehalose is crystalline trehalose hydrate or anhydrous crystalline trehalose.

20. The method of claim 9 wherein said saccharide composition comprises said non-reducing saccharide and at least one saccharide selected from the group consisting of trehalose and non-reducing saccharides bearing at the end a trehalose structure.

21. The method of claim 20 wherein said trehalose is crystalline trehalose hydrate or anhydrous crystalline trehalose.

22. The saccharide composition of claim 4, wherein said other saccharides are selected from the group consisting of trehalose and non-reducing saccharides bearing at the end a trehalose structure.

* * * * *